(12) United States Patent
Matlock et al.

(10) Patent No.: US 10,639,462 B2
(45) Date of Patent: May 5, 2020

(54) DILATION SYSTEM

(71) Applicant: Acclarent, Inc., Irvine, CA (US)

(72) Inventors: George L. Matlock, Pleasanton, CA (US); Don Q. Ngo-Chu, Irvine, CA (US); Randy S. Chan, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 378 days.

(21) Appl. No.: 15/296,255

(22) Filed: Oct. 18, 2016

(65) Prior Publication Data

US 2018/0104461 A1 Apr. 19, 2018

(51) Int. Cl.
*A61M 25/01* (2006.01)
*A61M 29/02* (2006.01)
(Continued)

(52) U.S. Cl.
CPC ............. *A61M 29/02* (2013.01); *A61B 1/233* (2013.01); *A61B 18/04* (2013.01); *A61M 25/0026* (2013.01); *A61M 25/0074* (2013.01); *A61M 25/0097* (2013.01); *A61M 25/0133* (2013.01); *A61M 25/0158* (2013.01); *A61B 17/24* (2013.01); *A61B 2018/0022* (2013.01); *A61B 2018/00327* (2013.01); *A61B 2018/046* (2013.01); *A61M 25/0032* (2013.01); *A61M 25/0041* (2013.01); *A61M 25/0136* (2013.01); *A61M 25/0138* (2013.01); *A61M 25/0147* (2013.01); *A61M 25/0155* (2013.01); *A61M 25/10182* (2013.11); *A61M 25/10187* (2013.11); *A61M 2025/0681* (2013.01);
(Continued)

(58) Field of Classification Search
CPC .............. A61M 29/02; A61M 25/0026; A61M 25/0133; A61M 25/0105; A61M 25/0158; A61M 25/0155; A61M 25/09141; A61M 2025/0036; A61M 2025/0037; A61M 2025/0039; A61B 2018/046; A61B 2018/00023; A61B 2017/003
See application file for complete search history.

(56) References Cited

U.S. PATENT DOCUMENTS 5,415,637 A * 5/1995 Khosravi ............ A61M 25/003
604/105
5,496,271 A * 3/1996 Burton ................... A61B 18/18
604/101.05

(Continued)

OTHER PUBLICATIONS

International Search Report and Written Opinion dated Mar. 12, 2018 for International Application No. PCT/US2017/055747, 21 pages.

(Continued)

*Primary Examiner* — Eun Hwa Kim
*Assistant Examiner* — Adam Z Minchella
(74) *Attorney, Agent, or Firm* — Frost Brown Todd LLC

(57) ABSTRACT

A catheter includes an articulation assembly that enables the distal end of the catheter to bend away from the longitudinal axis of a proximal portion of the catheter. The catheter may include a dilation catheter or a guide catheter. The articulation assembly may provide bending in response to changes in electrical current and/or in response to changes in temperature. In addition, or in the alternative, the articulation assembly may provide bending in response to translation of a wire member.

20 Claims, 21 Drawing Sheets

(51) Int. Cl.
*A61M 25/00* (2006.01)
*A61B 1/233* (2006.01)
*A61B 18/04* (2006.01)
*A61B 17/24* (2006.01)
*A61M 25/06* (2006.01)
*A61M 25/09* (2006.01)
*A61M 25/10* (2013.01)
*A61B 18/00* (2006.01)

(52) U.S. Cl.
CPC ............. *A61M 2025/09083* (2013.01); *A61M 2025/09116* (2013.01); *A61M 2025/09125* (2013.01); *A61M 2025/09175* (2013.01)

(56) References Cited

U.S. PATENT DOCUMENTS

| | | | | |
|---|---|---|---|---|
| 5,520,644 | A * | 5/1996 | Imran | A61M 25/0144 338/128 |
| 5,899,882 | A * | 5/1999 | Waksman | A61M 25/1002 604/103.07 |
| 9,155,492 | B2 | 10/2015 | Jenkins et al. | |
| 2003/0093105 | A1* | 5/2003 | Huffmaster | A61B 17/12113 606/192 |
| 2004/0116848 | A1* | 6/2004 | Gardeski | A61M 25/0147 604/95.01 |
| 2006/0064055 | A1* | 3/2006 | Pile-Spellman | A61M 25/0105 604/95.05 |
| 2007/0073098 | A1* | 3/2007 | Lenker | A61B 17/12 600/30 |
| 2007/0250036 | A1* | 10/2007 | Volk | A61M 25/0009 604/510 |
| 2007/0250104 | A1* | 10/2007 | Condrea | A61M 25/1011 606/193 |
| 2008/0147000 | A1* | 6/2008 | Seibel | A61M 25/0155 604/98.01 |
| 2008/0177142 | A1* | 7/2008 | Roskopf | A61B 1/00082 600/115 |
| 2008/0183128 | A1 | 7/2008 | Morriss et al. | |
| 2009/0125042 | A1* | 5/2009 | Mouw | A61B 17/1114 606/153 |
| 2010/0010437 | A1 | 1/2010 | Miles et al. | |
| 2010/0030031 | A1 | 2/2010 | Goldfarb et al. | |
| 2011/0004057 | A1 | 1/2011 | Goldfarb et al. | |
| 2012/0191076 | A1* | 7/2012 | Voegele | A61B 17/07207 606/1 |
| 2012/0323174 | A1 | 12/2012 | Shih | |
| 2014/0074141 | A1 | 3/2014 | Johnson et al. | |
| 2014/0213971 | A1* | 7/2014 | Dolan | A61F 2/82 604/104 |
| 2016/0001044 | A1* | 1/2016 | Rauch | A61M 25/0158 606/108 |
| 2016/0045719 | A1* | 2/2016 | Ha | A61M 29/02 606/196 |
| 2016/0175039 | A1* | 6/2016 | Aujla | A61M 25/0158 606/41 |
| 2016/0250444 | A1* | 9/2016 | Lampropoulos | A61M 25/0026 600/486 |

OTHER PUBLICATIONS

International Preliminary Report on Patentability dated Apr. 23, 2019 for International Application No. PCT/US2017/055747, 11 pages.

* cited by examiner

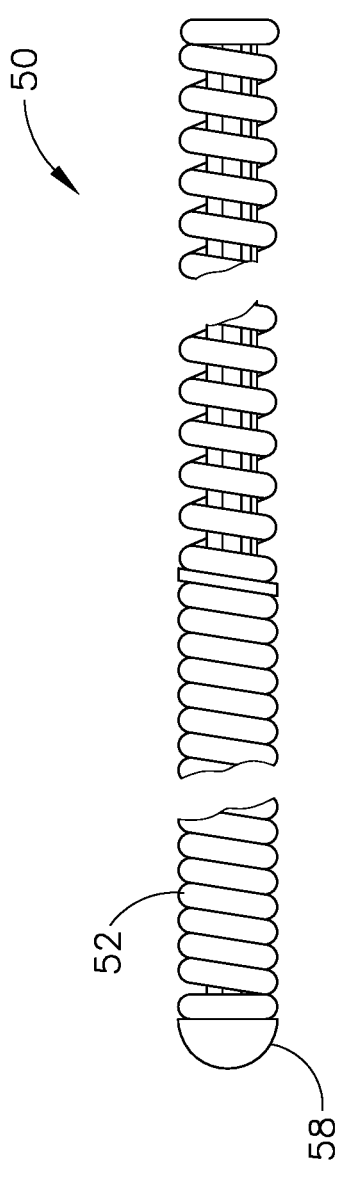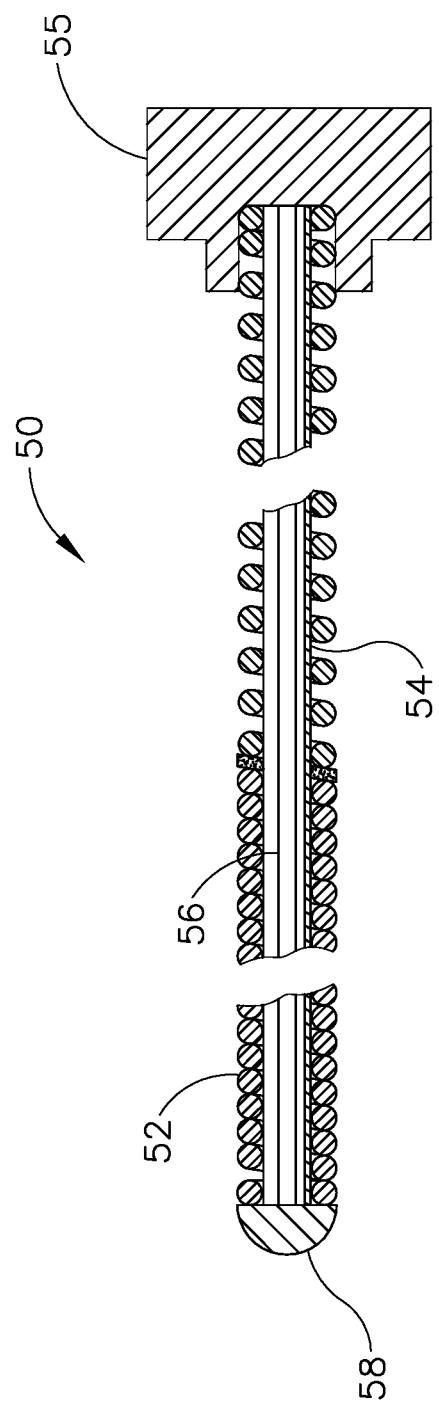
Fig. 3
Fig. 4

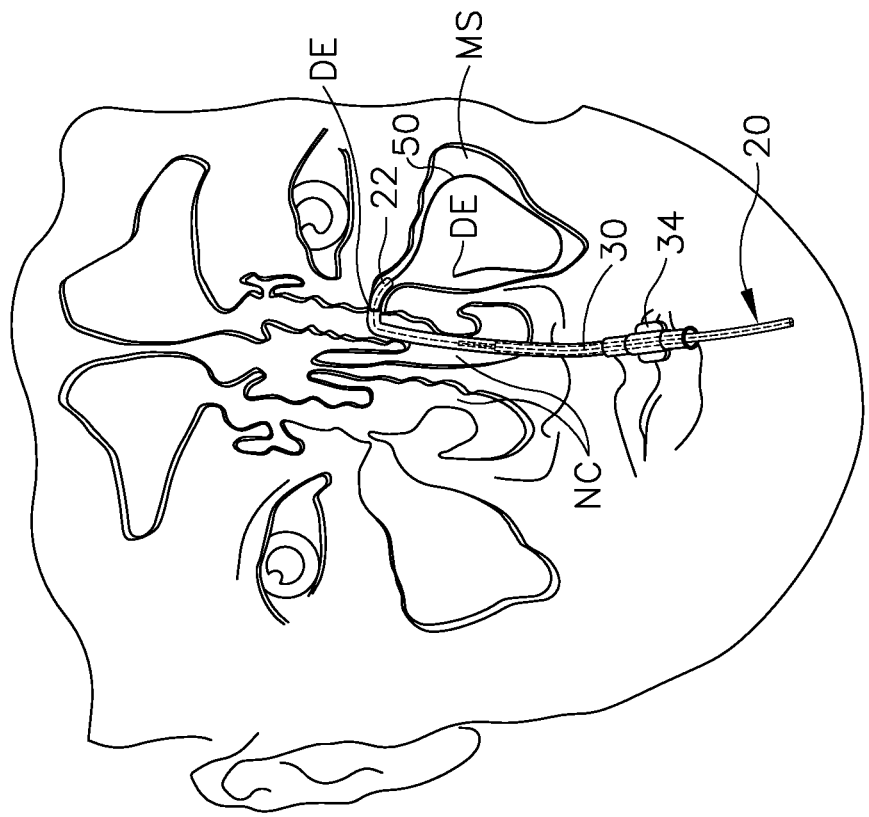
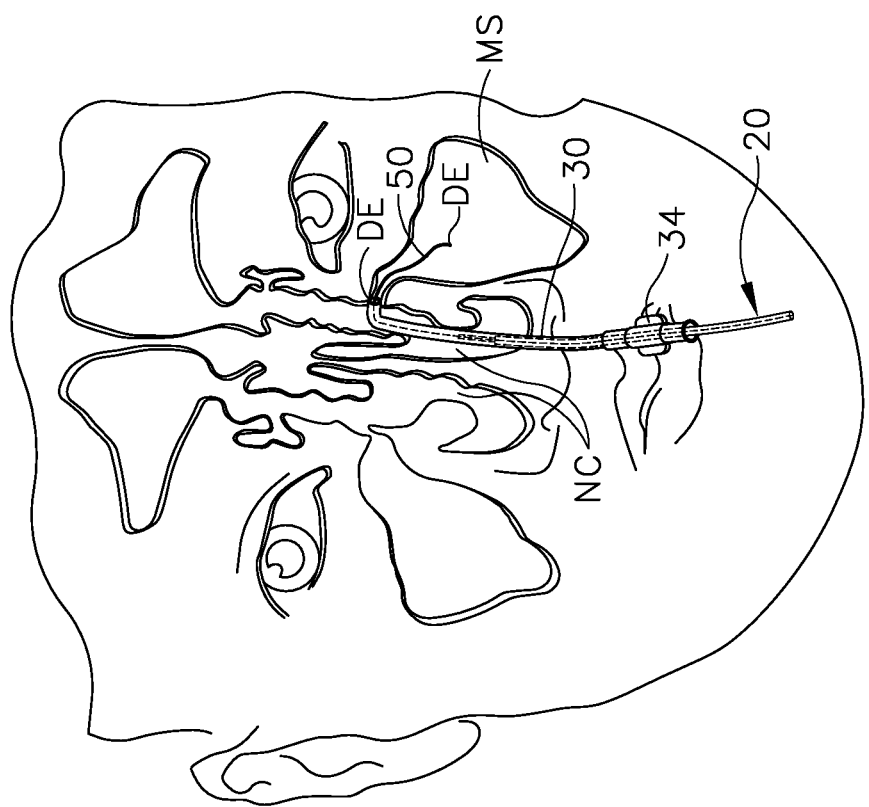
Fig. 7C
Fig. 7B

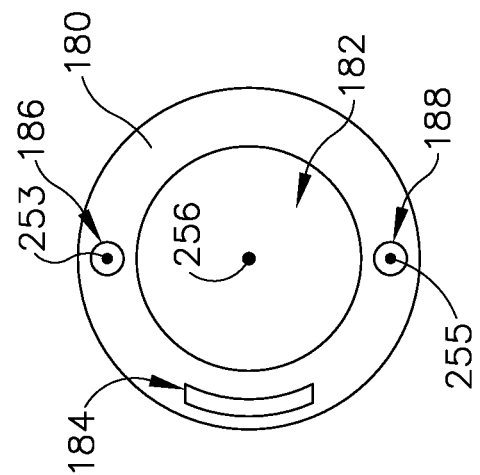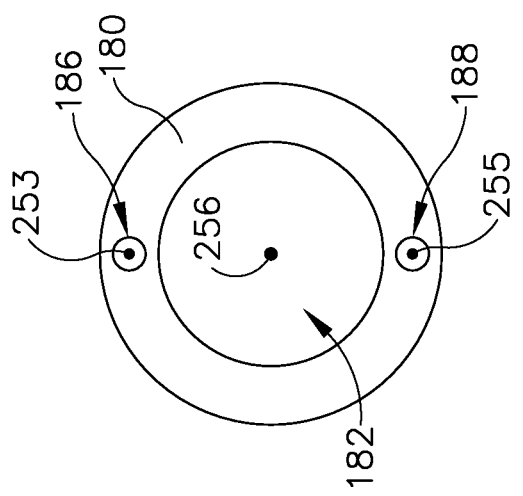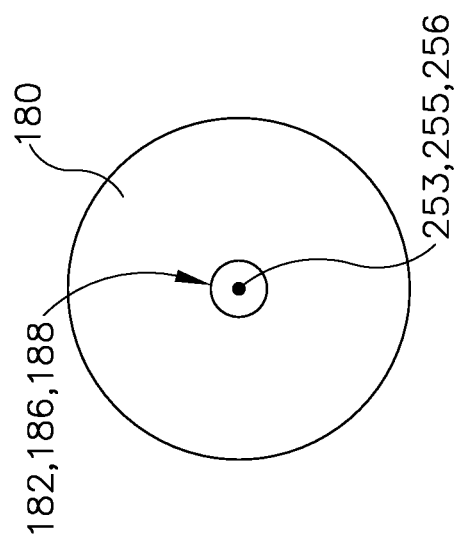

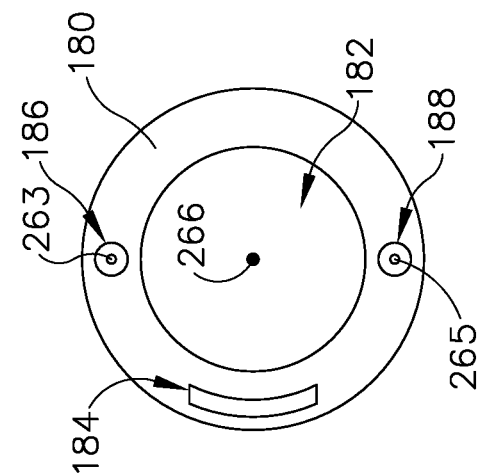
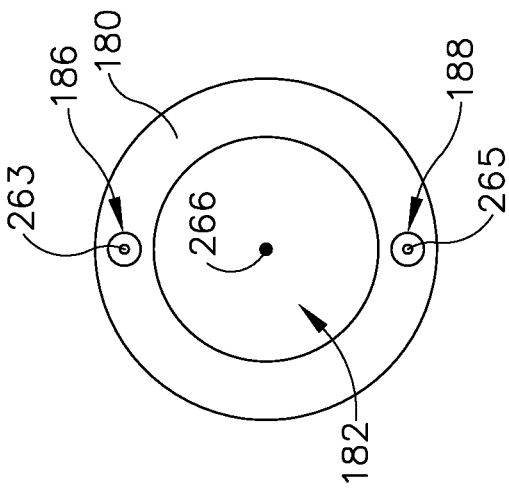
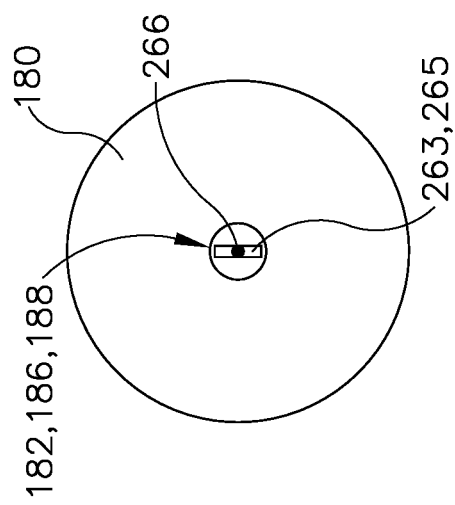

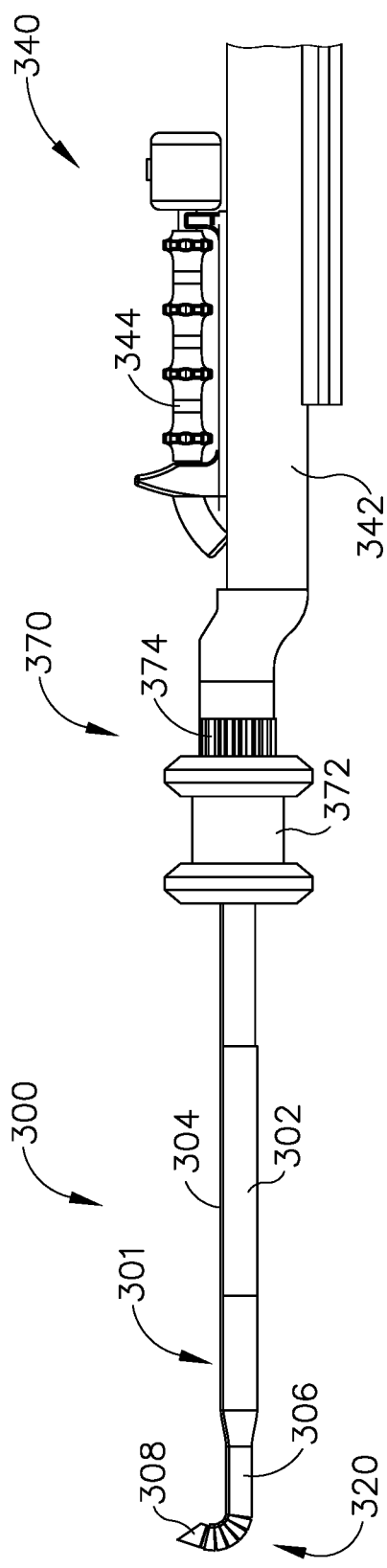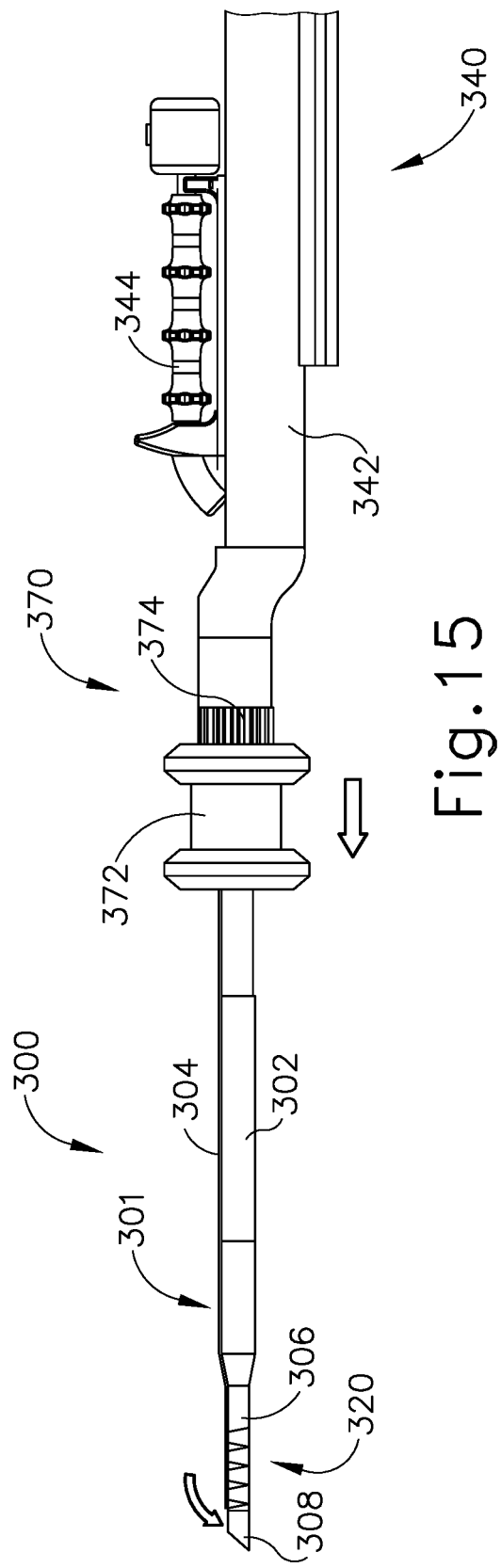

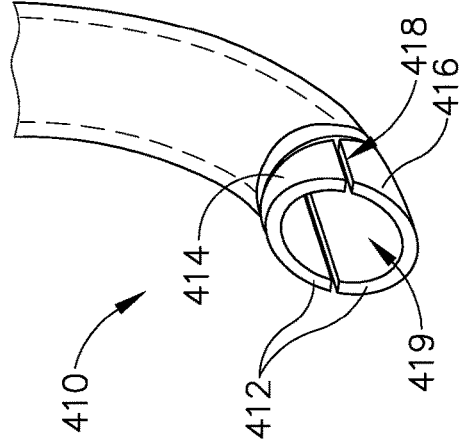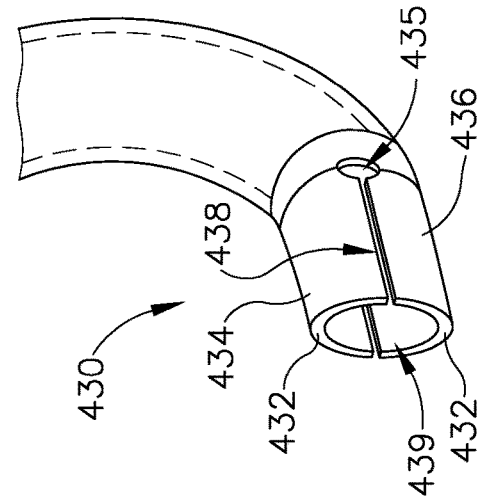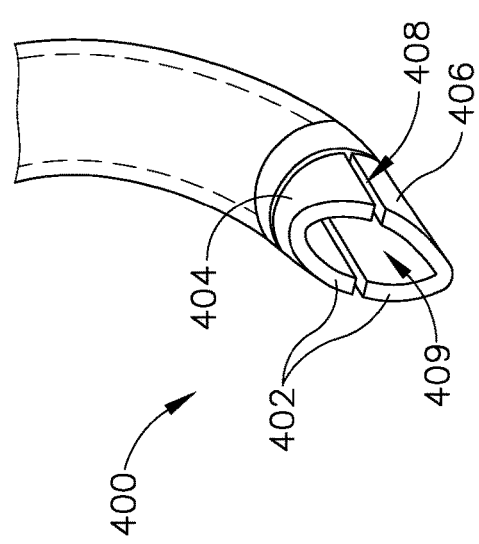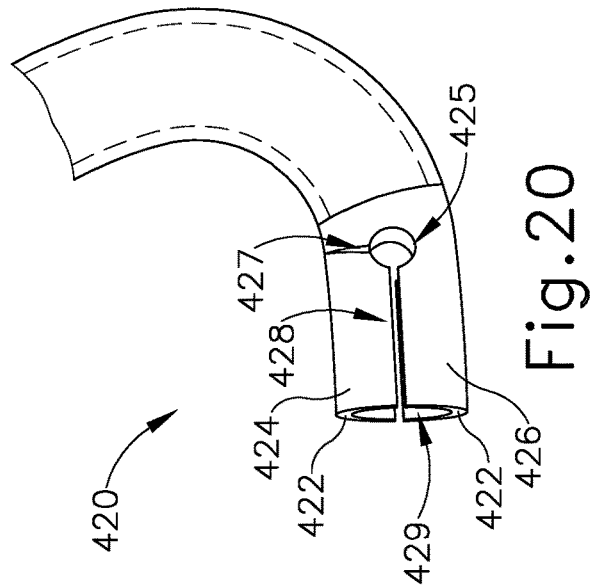

DILATION SYSTEM

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled placement of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a detailed side elevational view of the illuminating guide wire of FIG. 2A;

FIG. 4 depicts a detailed side cross-sectional view of the illuminating guidewire of FIG. 2A;

FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus;

FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus;

FIG. 9A depicts a cross-sectional view of the dilation catheter and distal articulation assembly of FIG. 8, taken along line 9A-9A of FIG. 8;

FIG. 9B depicts a cross-sectional view of the dilation catheter and distal articulation assembly of FIG. 8, taken along line 9B-9B of FIG. 8;

FIG. 9C depicts a cross-sectional view of the dilation catheter and distal articulation assembly of FIG. 8, taken along line 9C-9C of FIG. 8;

FIG. 12A depicts a cross-sectional view of the dilation catheter of FIG. 8 and the distal articulation assembly of FIG. 11, taken along line 12A-12A of FIG. 11;

FIG. 12B depicts a cross-sectional view of the dilation catheter of FIG. 8 and the distal articulation assembly of FIG. 11, taken along line 12B-12B of FIG. 11;

FIG. 12C depicts a cross-sectional view of the dilation catheter of FIG. 8 and the distal articulation assembly of FIG. 11, taken along line 12C-12C of FIG. 11;

FIG. 14 depicts a side elevational view of an exemplary alternative guide catheter assembly having a bendable distal end, where the bendable distal end is in a first, bent, configuration;

FIG. 15 depicts a side elevational view of the guide catheter assembly of FIG. 14, where the bendable distal end is in a second, straight, configuration;

FIG. 18 depicts a perspective view of an alternative tip that may be readily incorporated into the guide catheter of FIG. 16 or the guide catheter of FIG. 2B;

FIG. 19 depicts a perspective view of another alternative tip that may be readily incorporated into the guide catheter of FIG. 16 or the guide catheter of FIG. 2B;

FIG. 20 depicts a perspective view of another alternative tip that may be readily incorporated into the guide catheter of FIG. 16 or the guide catheter of FIG. 2B;

FIG. 21 depicts a perspective view of another alternative tip that may readily incorporated into the guide catheter of FIG. 16 or the guide catheter of FIG. 2B;

Figure 1:
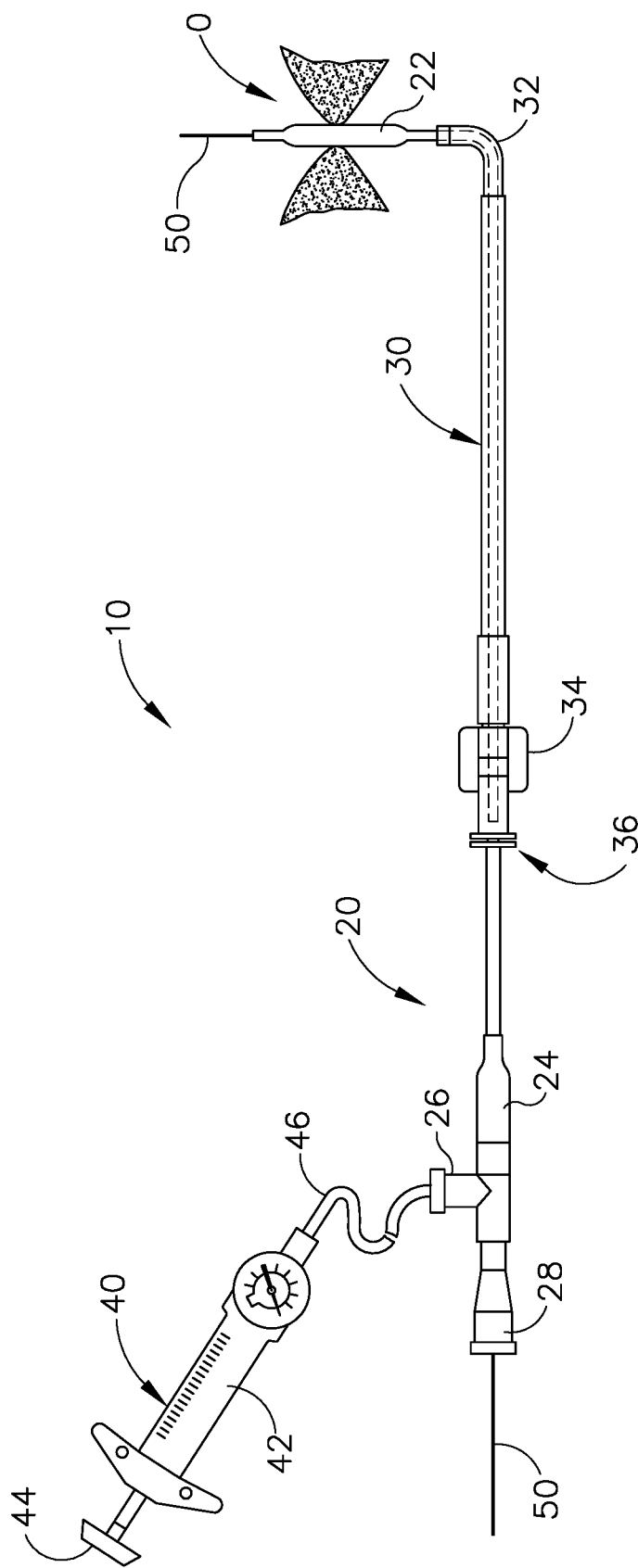
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

Figure 2A:
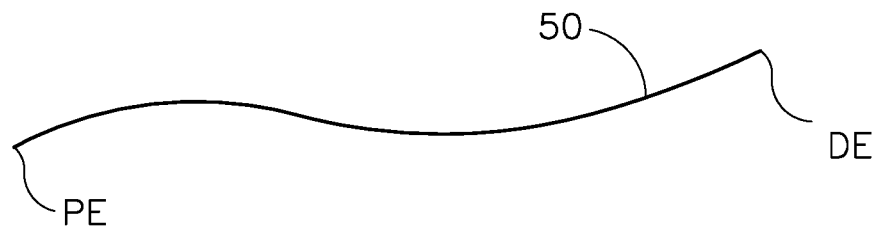
FIG. 2A depicts a side elevational view of an exemplary illuminating guidewire of the dilation catheter system of FIG. 1.
Figure 2B:
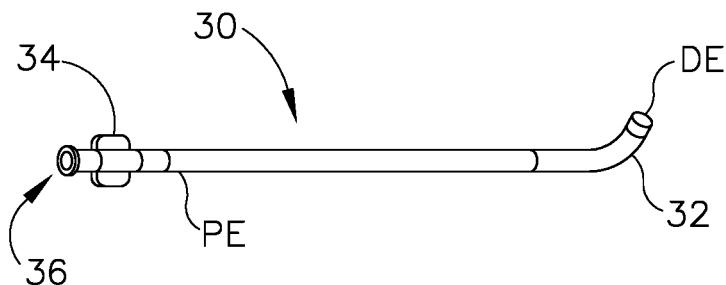
FIG. 2B depicts a side elevational view of an exemplary guide catheter of the dilation catheter system of FIG. 1.
Figure 2C:
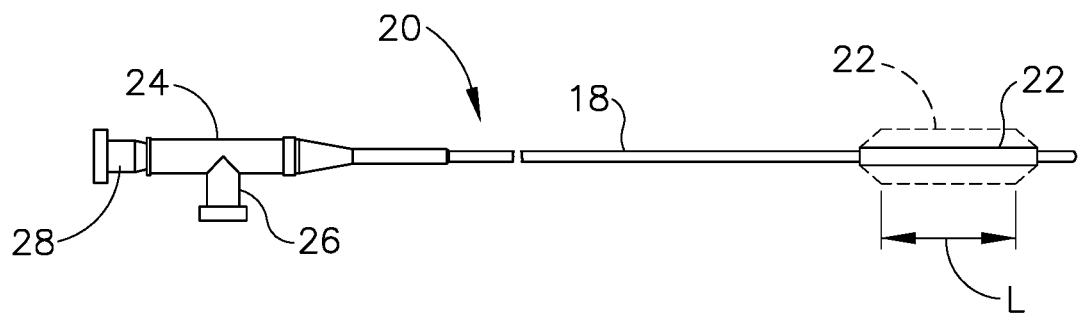
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22).

Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

II. Overview of Exemplary Endoscope

Figure 5:
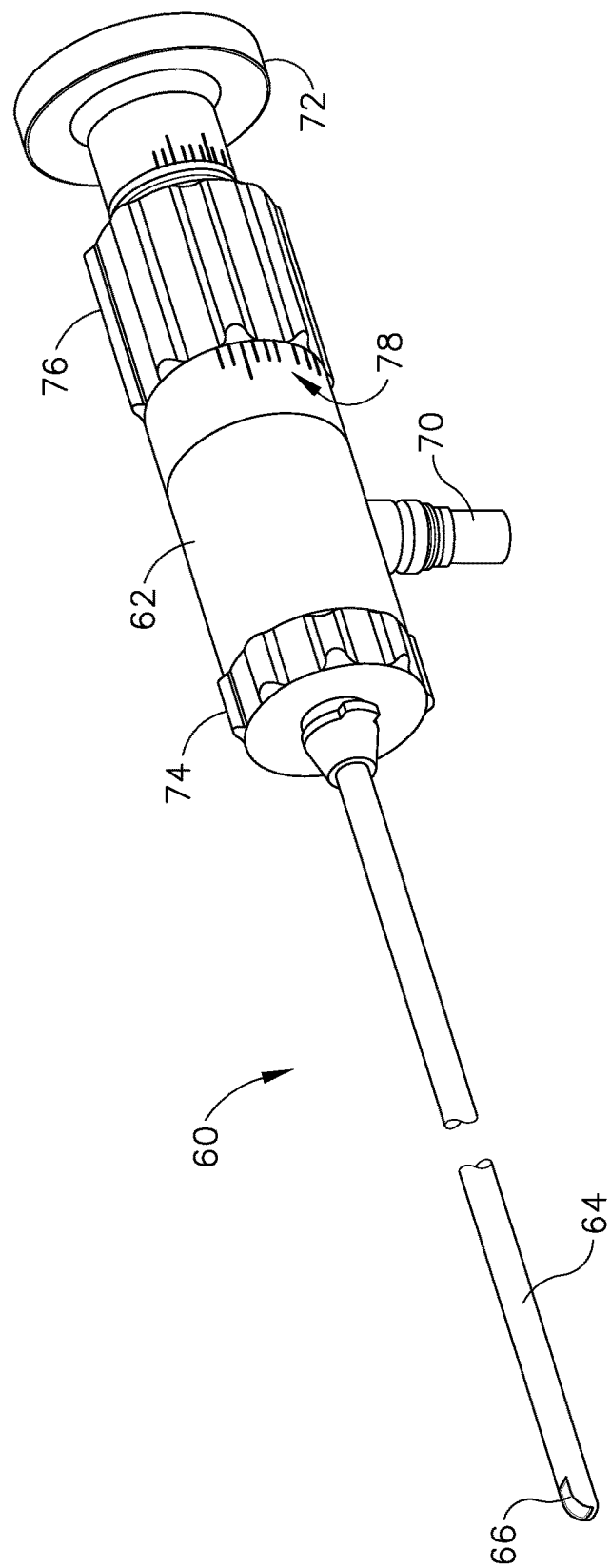
FIG. 5 depicts a perspective view of an exemplary endoscope suitable for use with the dilation catheter system of FIG. 1.
Figure 6:
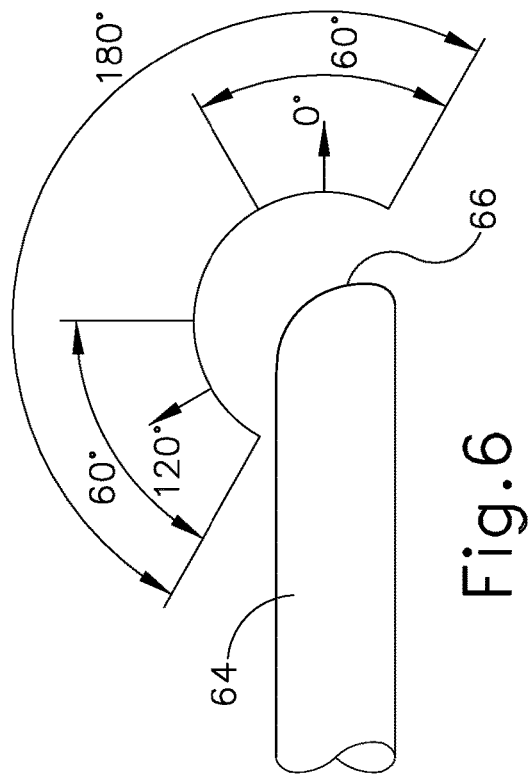
FIG. 6 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein

III. Exemplary Method for Dilating the Ostium of a Maxillary Sinus

FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7A:
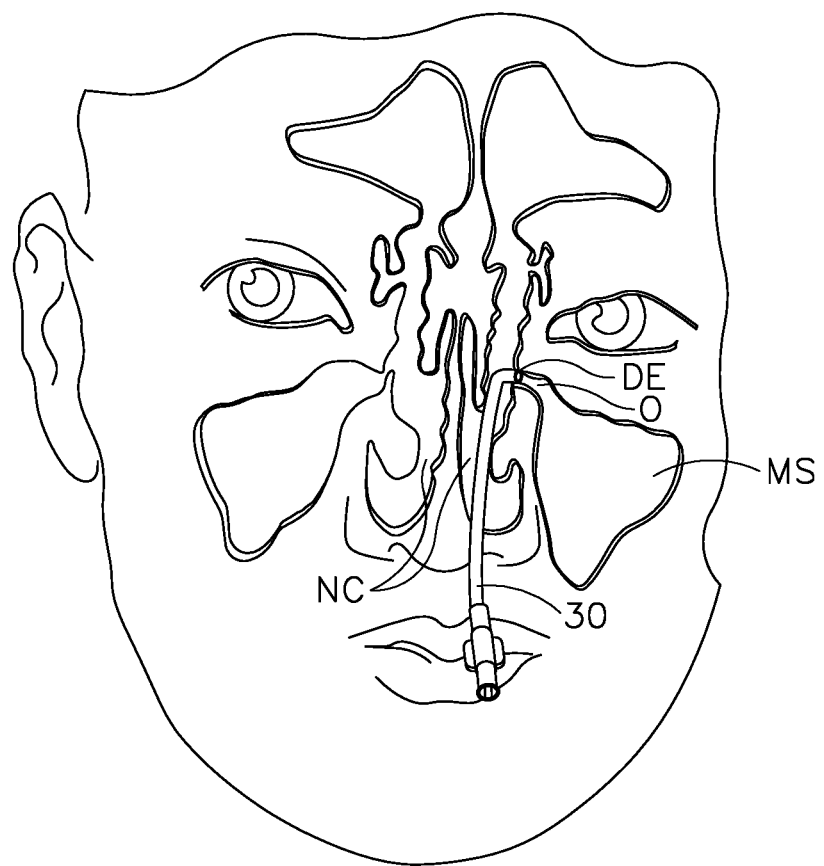
FIG. 7A depicts a front view of the guide catheter of FIG. 2B positioned adjacent an ostium of the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7E:
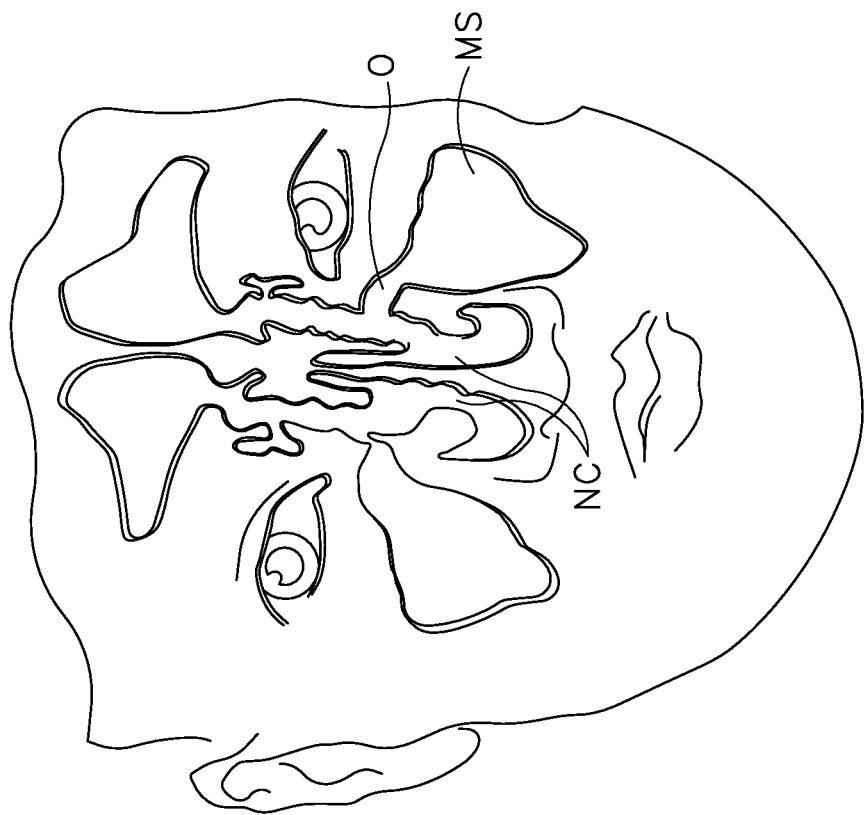
FIG. 7E depicts a front view of an ostium of the maxillary sinus, with the ostium having been enlarged by inflation of the balloon of FIG. 7D.
Figure 7D:
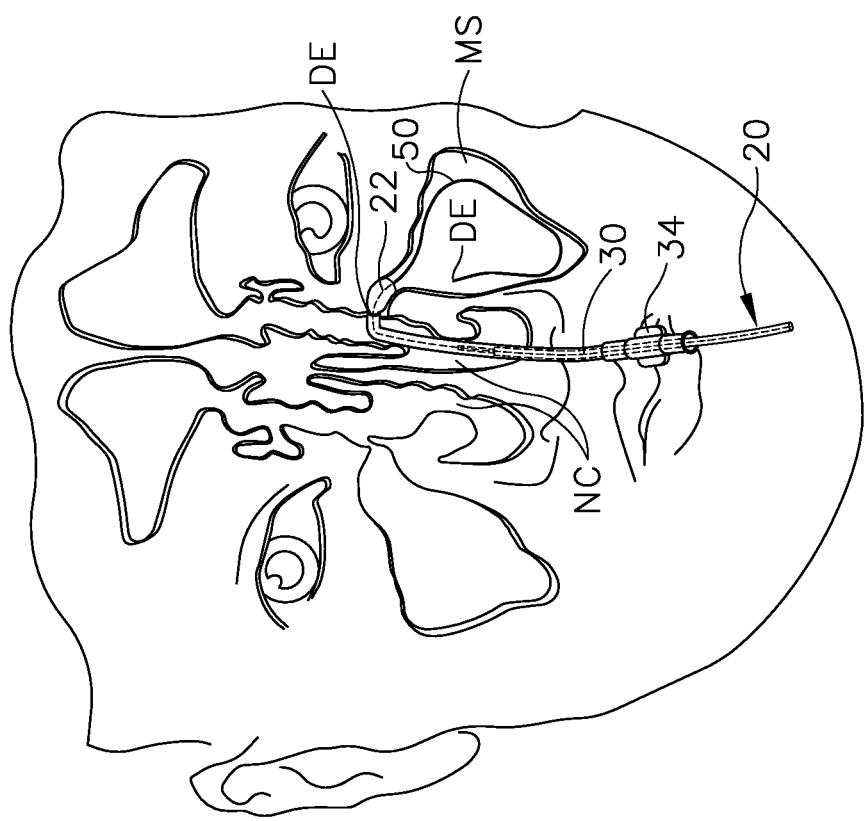
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (O). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," now abandoned, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

IV. Exemplary Alternative Dilation Catheter with Distal Articulation Assembly In some instances, it may be desirable to articulate/bend the distal end of a dilation catheter from the longitudinal axis defined by the rest of the dilation catheter. It may further be desirable to selectively articulate/bend the distal end of a dilation catheter during a dilation procedure at various angles while the distal end of the dilation catheter is adjacent to a targeted area. In other words, it may be desirable to bend the distal end of the dilation catheter while the dilation catheter is within an anatomical passageway of a patient. Selective articulation/bending of the distal end of a dilation catheter during a procedure may provide better steering capabilities within a nasal cavity of a patient, allowing an operator to more easily position a dilator within a targeted area. For instance, the operator may initially insert the catheter into the patient's nasal cavity while the catheter is in a straight configuration; then bend the distal end of the catheter after the catheter is positioned in the patient's nasal cavity. The bend angle may be selectively customized to facilitate access to a drainage passageway associated with a particular paranasal sinus cavity. For instance, the operator may selectively adjust the bend angle to access a drainage passageway associated with a frontal sinus, a maxillary sinus, a sphenoid sinus, or an ethmoid sinus. The following are exemplary dilation catheters having distal articulation assemblies that are configured to deflect a distal end of a dilation catheter located adjacent to a targeted area within a patient. While the following examples relate to articulation assemblies for dilation catheters, it should be understood that the same kinds of articulation assemblies may be readily incorporated into guide catheters and/or other kinds of catheters.

Figure 8:
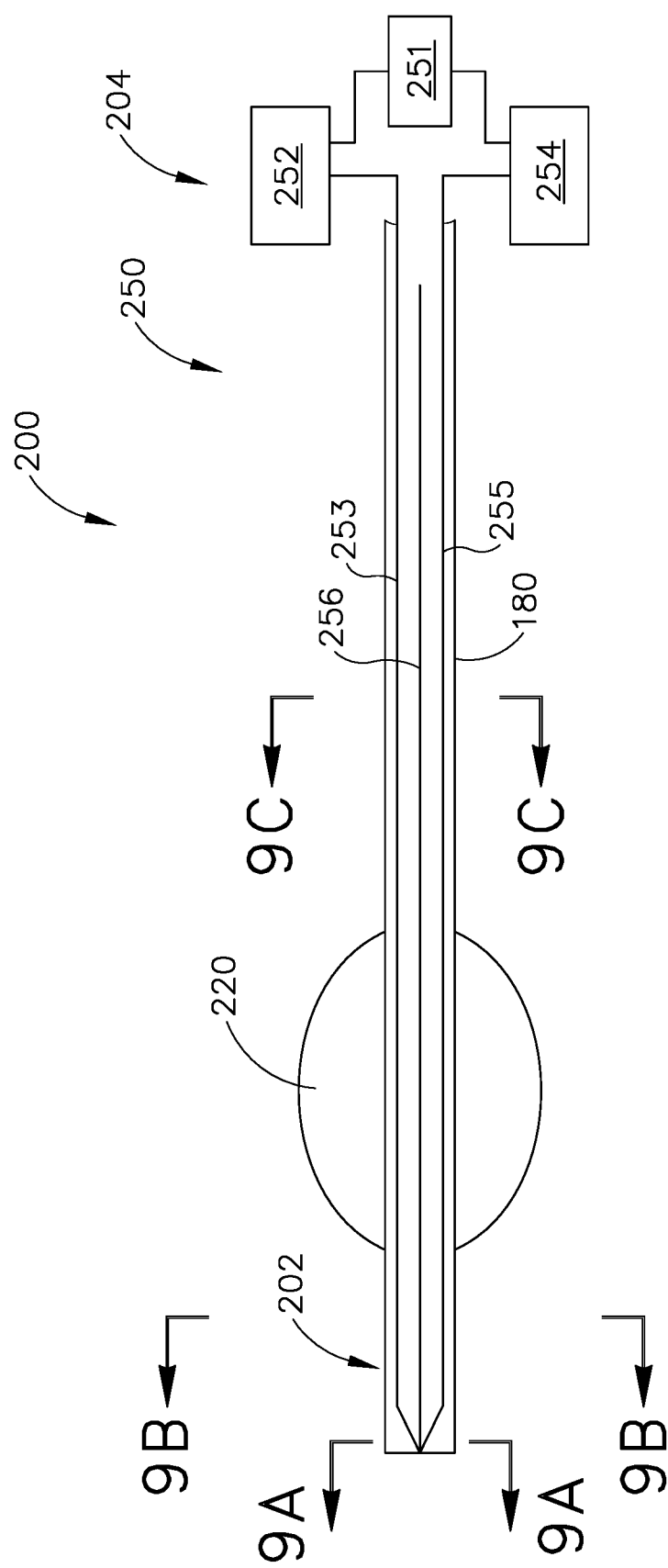
FIG. 8 depicts a side elevational view of an alternative dilation catheter coupled to a distal articulation assembly, both of which together may be readily incorporated into the dilation catheter system of FIG. 1 in place of the dilation catheter of FIG. 2C.

FIG. 8 shows an alternative dilation catheter (200) coupled with a distal articulation assembly (250). Dilation catheter (200) and distal articulation assembly (250) may be readily incorporated into dilation catheter system (10) in replacement of dilation catheter (20) as described above. As will be described in greater detail below, distal articulation assembly (250) is configured to selectively articulate a bendable distal end (202) of dilation catheter (200) at various desirable angles relative to the longitudinal axis defined by the rest of dilation catheter (200).

Dilation catheter (200) includes a hollow elongate shaft (180) coupled to a dilator (220). Hollow elongate shaft (180) and dilator (220) may be substantially similar to shaft (18) and dilator (22) described above, respectively, with differences described below. Hollow elongate shaft (180) extends from an open proximal end (204) to a bendable distal end (202). Open proximal end (204) may be substantially similar to open proximal end (28) described above. It should be understood that while distal end (202) is described as bendable; the entire length, or any other suitable length of hollow elongate shaft (180) may be sufficiently flexible as would be apparent to one having ordinary skill in the art in view of the teachings herein. As best shown in FIG. 9C, hollow elongate shaft (180) defines an inflation lumen (184) that extends from an open proximal end (204) of dilation catheter (200) and terminates within the interior of dilator (220). Therefore, similar to dilator (22) and shaft (18), dilator (220) may be selectively inflated and deflated by communicating fluid along inflation lumen (184) via lateral port (26).

As best shown in FIGS. 9A-9C, hollow elongated shaft (180) also defines a central lumen (182), an upper lumen (186), and a lower lumen (188). Central lumen (182), upper lumen (186), and lower lumen (188) extend from open proximal end (204) of elongated shaft (180) and converge within a portion of bendable distal end (202) distal relative to dilator (220). As will be described in greater detail below, central lumen (182), upper lumen (186), and lower lumen (188) converge so that selected portions of distal articulation assembly (250) extending through individual lumens (182, 186, 188) may come into contact at the point of convergence. In the current example, central lumen (182), upper lumen (184), and lower lumen (186) are isolated from each other along locations of hollow elongate shaft (180) shown in FIGS. 9B-9C. It should be understood that this is merely optional, as central lumen (182), upper lumen (186), and lower lumen (186) may be in communication with each other along any suitable length of hollow elongate shaft (180) as would be apparent to one having ordinary skill in the art in view of the teachings herein.

Distal articulation assembly (250) includes a power control unit (251) in electrical communication with a positive lead (252) and a negative lead (254), a lead resistive element (253) extending from positive lead (252) and within upper lumen (186), a return resistive element (255) extending from negative lead (254) and within lower lumen (188), and a steering member (256) extending within central lumen (182). Lead resistive element (253), return resistive element (255), and steering member (256) connect with each other along the length of hollow elongate shaft (180) where central lumen (182), upper lumen (184), and lower lumen (186) converge, as shown in FIG. 9A. Therefore, lead resistive element (253) and return resistive element (255) complete an electrical circuit between positive lead (252) and negative lead (254), while steering member (256) is in thermal communication with both lead resistive element (253) and return resistive element (255). In the current example, lead resistive element (253) and return resistive element (255) are two separate resistive elements, such as wires. However, lead resistive element (253) and return resistive element (255) may be one single resistive element or any other suitable number of resistive elements connected together as would be apparent to one having ordinary skill in the art.

Steering member (256) may increase stiffness, torquability, and steerability of the distal end of hollow elongate shaft (180). In the current example, a proximal end of steering member (256) terminates within hollow elongate shaft (180) near open proximal end (204). However, steering member (256) may have any suitable length as would be apparent to one having ordinary skill in the art in view of the teachings herein. For example, steering member (256) may terminate within central lumen (182) distally relative to dilator (220). In the current example, lead resistive element (253), return resistive element (255), and steering member (265) are connected with each other along hollow elongate shaft (180) at the position shown in FIG. 9A via welding. However, any suitable coupling means may be used as would be apparent to one having ordinary skill in the art in view of the teachings herein. Alternatively, steering member (256) may be in sufficient thermal communication with lead resistive element (253) and return resistive element (255) such that steering member (256) is not physically coupled with lead resistive element (252) and return resistive element (255) at all. As will be described in greater detail below, power control unit (251) may allow an operator to apply a selected current through lead resistive element (253) and return resistive element (255) in order to deflect a distal end of steering member (256) and bendable distal end (202) relative to the longitudinal axis defined by the rest of hollow elongate shaft (180).

Power control unit (251) is configured to generate a predetermined current through lead resistive element (253) and return resistive element (255). Lead resistive element (253) and return resistive element (255) act as resistor elements, such that current generated by power control unit (251) is converted into a predetermined amount of thermal energy due to suitable resistive properties of lead resistive element (253) and return resistive element (255). Upper lumen (186) and lower lumen (188) may be sufficiently insulated such that excess thermal energy does not conduct to the exterior of hollow elongate shaft, which may potentially discomfort the patient.

Power control unit (251) may be configured to operate at a plurality of settings, each having different predetermined currents associated with various thermal energy levels. In some such versions, different settings may be associated with different paranasal sinus cavities, such that the operator may select a particular setting via power control unit (251) based on the particular paranasal sinus cavity whose drainage passageway the operator wishes to dilate. Based on the operator's selection, power control unit (251) may activate steering member (256) to provide a bend angle that is tailored to facilitate access to the drainage passageway associated with the particular paranasal sinus cavity indicated by the operator's selection.

Power control unit (251) may include a variable resistor/constant voltage device, a resistance bridge, a plurality of user controls, and any other suitable components as would be apparent to one having ordinary skill in the art in view of the teachings herein. In the current example, power control unit (251) and leads (252, 254) are located exterior to hollow elongate shaft (180). It should be understood that power control unit (251) and leads (252, 254) may be incorporated into various suitable components of dilation catheter system (10), such as a handle configured to be grasped by an operator.

Figure 10:
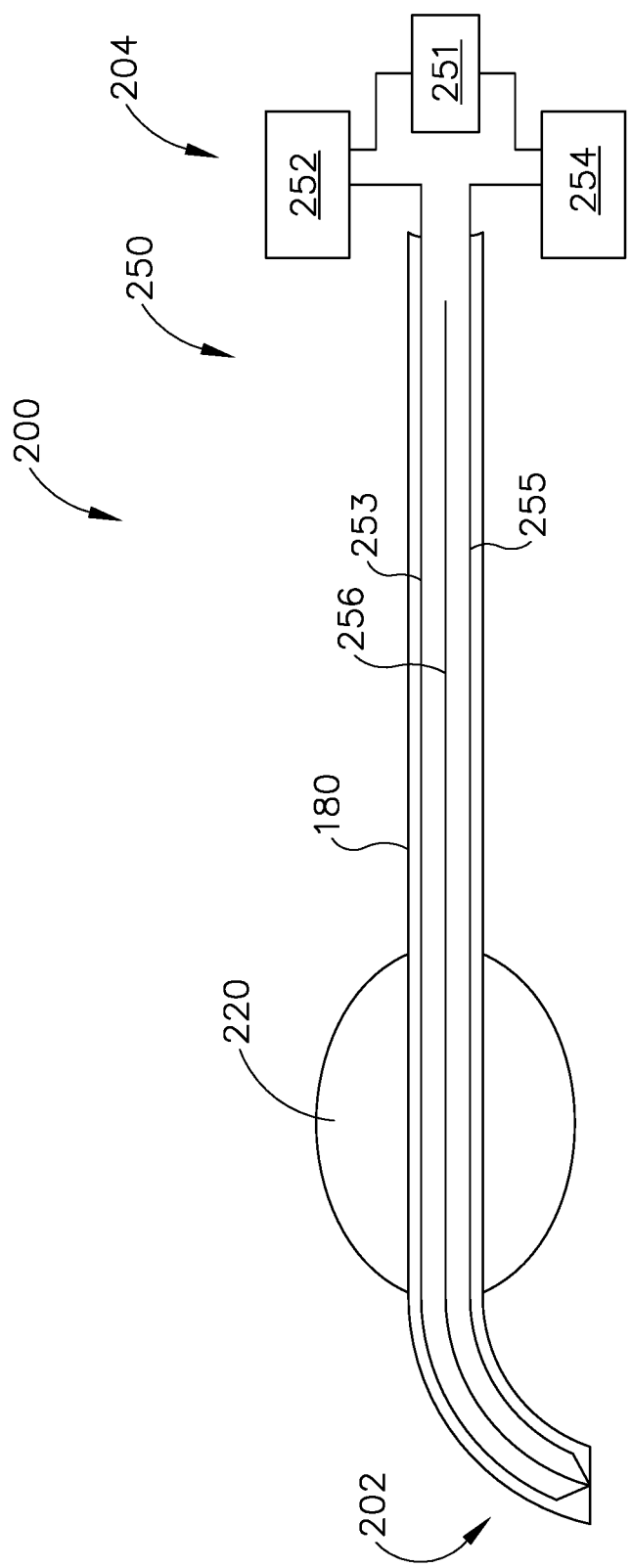
FIG. 10 depicts a side elevational view of the dilation catheter and the distal articulation assembly of FIG. 8, where a distal end of the dilation catheter is in an articulated position.

Steering member (256) is made out of any suitable material designed to convert temperature change into mechanical displacement. As noted above, the distal end of steering member (256) is in thermal communication with lead resistive element (253) and return resistive element (255). Therefore, when power control unit (251) generates current through lead resistive element (253) and return resistive element (255), the generated thermal energy is absorbed by steering member (256) at the longitudinal location shown in FIG. 9A. The absorbed thermal energy by steering member (256) causes the distal end of steering member (256) to deflect relative to the longitudinal axis of hollow elongate shaft (180). The deflected distal end of steering member (256) makes contact with the interior wall of central lumen (182) such that bendable distal end (202) also deflects with the distal end of steering member (256), as shown in FIG. 10. As a result, an operator may selectively articulate bendable distal end (202) through activation of power control unit (251).

The current example shows steering member (256) placed within central lumen (182) such that steering member (256) and central lumen (182) do not come into contact with each other when steering member (256) is parallel with the longitudinal axis of hollow elongate shaft (180). However, this is merely optional, as steering member (256) and central lumen (182) may be dimensioned for constant contact with each other through tighter tolerances. Additionally, steering member (256) may be fixed within central lumen (182) through an interference fit or any other suitable coupling means that would be apparent to one having ordinary skill in the art in view of the teachings herein.

As mentioned above, power control unit (251) may include a plurality of electrical current settings correlating to different thermal settings of resistive elements (253, 255). Different thermal settings may result in different temperature changes within steering member (256), which results in different deflection angles relative to the longitudinal axis of hollow elongate shaft (180). Therefore, an operator may selectively articulate bendable distal end at a variety of deflection angles through a plurality of electrical current settings of power control unit (251). Steering member (256) may include a pre-formed nitinol bi-phase wire, strip or foil. If steering member (256) is made with a pre-formed nitinol bi-phase material, distal bendable end (202) may obtain a straight angle relative to the longitudinal axis of shaft (180), and two bent angles. Alternatively, steering member (256) may comprise a bi-metallic wire, strip or foil composition. If steering member (256) is made with a bi-metallic material, distal bendable end (202) may obtain a straight angle relative to the longitudinal axis of shaft (180) as well as a plurality of bent angles. Steering member (256) may be made out of any suitable combination of materials designed to convert temperature change into mechanical displacement.

As another merely illustrative example, steering member (256) and/or elements (253, 254) may comprise an electroactive polymer and/or other materials that are configured to expand or contract in response to an electrical current, without necessarily providing expansion, contraction, or other movement in response to changes in temperature. Other suitable kinds of components that may be used to provide steering member (256) and/or elements (253, 254) will be apparent to those of ordinary skill in the art in view of the teachings herein.

In exemplary use, an operator may place the distal end of dilation catheter (200) and distal articulation assembly (250) within the nasal cavity of a patient. The operator may desire to articulate the already inserted bendable distal end (202) of shaft (180) in order to align the tip of bendable distal end (202) with a targeted ostium or other drainage passageway of the patient. The operator may then adjust power control unit (251) to provide a desired current through lead resistive element (253) and return resistive element (255), which in turn heats and articulates bendable distal end (202) to align with the targeted ostium or other drainage passageway of the patient (similar to that shown from the transition of FIG. 8 to FIG. 10). With the tip of bendable distal end (202) aligned with the targeted ostium or other drainage passageway of the patient, the an operator may further insert bendable distal end (202) into the targeted ostium or other drainage passageway such that dilator (220) is adjacent with the targeted ostium or other drainage passageway. It should be understood that steering member (256) may not only articulate bendable distal end (202), but may also provide increased stiffness, torquability, and steerability such that bendable distal end (202) may be more easily inserted into the targeted ostium or other drainage passageway. With dilator (220) placed within the targeted ostium, the operator may inflate dilator (202) via communication fluid and inflation lumen (184). With the targeted ostium or other drainage passageway dilated, the operator may deflate dilator (202) and remove dilation catheter (200) from the patient.

Figure 11:
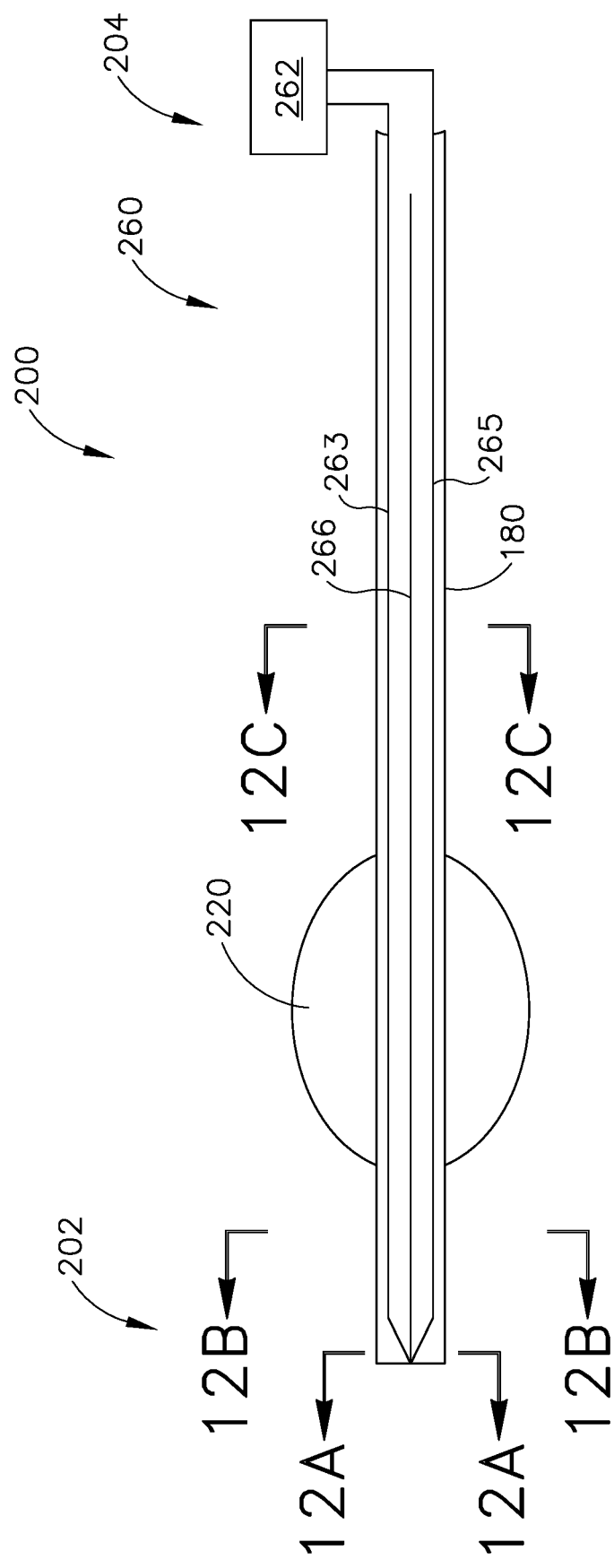
FIG. 11 depicts a side elevational view of the dilation catheter of FIG. 8 coupled to an alternative distal articulation assembly, both of which together may be readily incorporated into the dilation catheter system of FIG. 1 in place of the dilation catheter of FIG. 2C.

FIG. 11 shows dilation catheter (200) coupled to an alternative distal articulation assembly (260). Dilation catheter (200) and alterative distal articulation assembly (260) may be readily incorporated into dilation catheter system (10) in replacement of dilation catheter (20) as described above. As will be described in greater detail below, distal articulation assembly (260) is configured to selectively articulate bendable distal end (202) of dilation catheter (200) at various desirable angles relative to the longitudinal axis defined by the rest of dilation catheter (200).

Similar to distal articulation assembly (250), central lumen (182), upper lumen (186), and lower lumen (188) are dimensioned to house selected portioned of alternative distal articulation assembly (260) such that selected portions of alternative distal articulation assembly (260) come into contact with each other at the location of shaft (180) shown in FIG. 12A.

Alternative distal articulation assembly (260) includes a fluid circulation assembly (262), a lead fluid tube (263) extending from fluid circulation assembly (262) and within upper lumen (186), a return fluid tube (265) extending from fluid circulation assembly (262) and within lower lumen (188), and a steering member (266) extending within central lumen (182). Lead fluid tube (263), return fluid tube (265), and steering member (266) connect with each other along the length of hollow elongated shaft (180) where central lumen (182), upper lumen (184), and lower lumen (186) converge, as shown in FIG. 12A. Therefore, lead fluid tube (263) and return fluid tube (265) complete a fluid circuit with fluid circulation assembly (262), while steering member (266) is in thermal communication with both lead fluid tube (263) and return fluid tube (265).

Steering member (266) may increase stiffness, torquability, and steerability of the distal end of hollow elongate shaft (180). In the current example, a proximal end of steering member (266) terminates within hollow elongate shaft (180) near open proximal end (204). However, steering member (266) may have any suitable length as would be apparent to one having ordinary skill in the art in view of the teachings herein. For example, steering member (266) may terminate within central lumen (182) distally relative to dilator (220). Steering member (266) may be connected with lead fluid tube (263) and return fluid tube (265) by any suitable coupling means may be used as would be apparent to one having ordinary skill in the art in view of the teachings herein. Alternatively, steering member (266) may be in sufficient thermal communication with lead fluid tube (263) and return fluid tube (265) such that steering member (266) is not physically coupled with fluid tubes (263, 265) at all. As will be described in greater detail below, fluid circulation assembly (262) may allow an operator to heat/cool any suitable thermal fluid and pump the thermal fluid through lead fluid tube (262) and return fluid tube (265) in order to deflect a distal end of steering member (266) and bendable distal end (202) relative to the longitudinal axis defined by the rest of hollow elongate shaft (180).

Fluid circulation assembly (262) may be configured to heat/cool the suitable thermal fluid at a plurality of temperatures and pump the thermal fluid through fluid tubes (263, 265) in a cyclical manner. Fluid circulation assembly (262) may include any variety of heating/cooling elements, pumping mechanisms, valves, reservoirs, or other suitable components that would be apparent to one having ordinary skill in the art in view of the teachings herein. In the current example, fluid circulation assembly (262) is located exterior to hollow elongate shaft (180). It should be understood that fluid circulation assembly (262) may be incorporated into various suitable components of dilation catheter system (10), such as a handle configured to be grasped by an operator.

Figure 13:
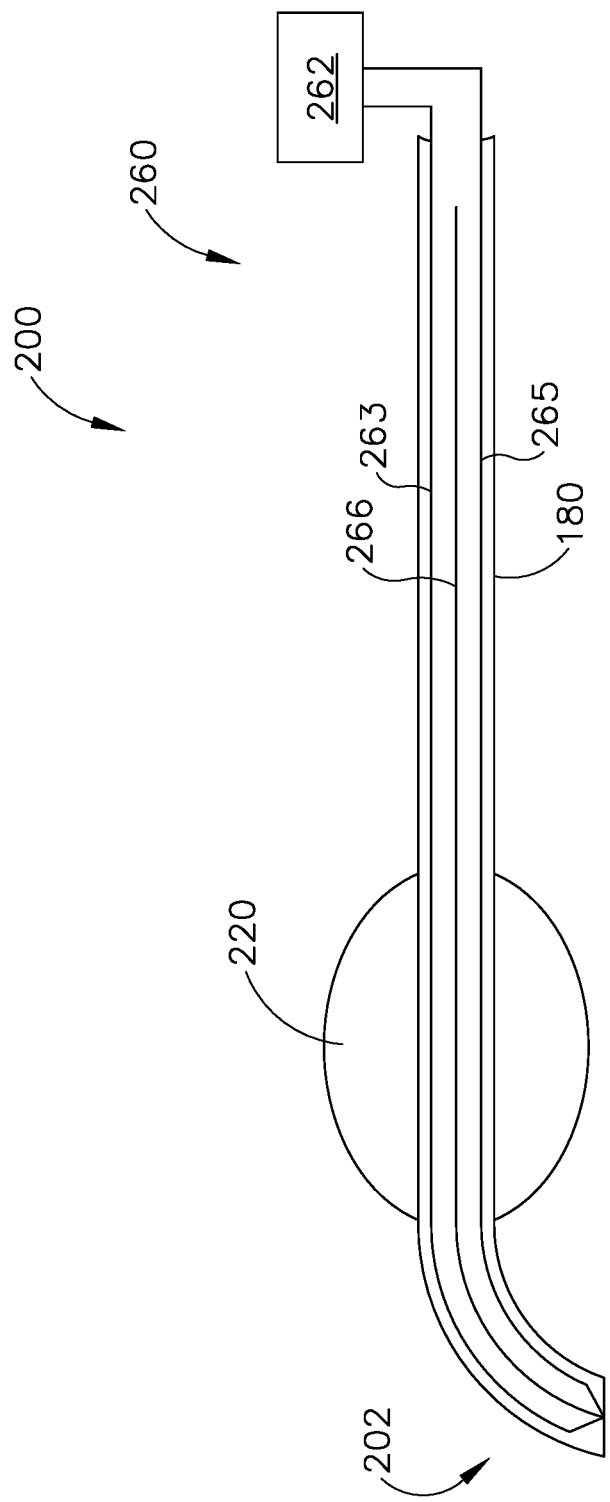
FIG. 13 depicts a side elevational view of the dilation catheter of FIG. 8 and the articulation assembly of FIG. 11, where the distal end of the dilation catheter is in an articulated position.

Steering member (266) may be substantially similar to steering member (256) described above. Therefore, steering member (266) may be made out of any suitable material designed to convert temperature change into mechanical displacement. As noted above, the distal end of steering member (266) is in thermal communication with lead fluid tube (263) and return fluid tube (265). Therefore, when fluid circulation assembly (262) heats/cools the suitable thermal fluid and pumps the thermal fluid through tubes (263, 265), thermal energy is transferred from the thermal fluid within fluid tubes (263, 265) to steering member (266) at the longitudinal location shown in FIG. 9A. The absorbed thermal energy by steering member (266) causes the distal end of steering member (256) to deflect relative to the longitudinal axis of hollow elongate shaft (180). Of course, the thermal fluid may be cooled to a temperature less that steering member (266) such that steering member (266) transfers thermal energy to thermal fluid. The deflected distal end of steering member (266) makes contact with the interior wall of central lumen (182) such that bendable distal end (202) also deflects with the distal end of steering member (266), as shown in FIG. 13. As a result, an operator may selectively articulate bendable distal end (202) through activation of fluid circulation assembly (62).

The current example shows steering member (266) placed within central lumen (182) such that steering member (266) and central lumen (182) do not come into contact with each other. However, this is merely optional, as steering member (266) and central lumen (182) may be dimensioned for constant contact with each other through tighter tolerances. Additionally, steering member (266) may be fixed within central lumen (182) through an interference fit or any other suitable coupling means that would be apparent to one having ordinary skill in the art in view of the teachings herein.

As mentioned above, fluid circulation assembly (262) may include features to heat/cool thermal fluid to a variety of desired temperatures. Different temperatures of thermal fluid may result in different temperature changes within steering member (266), which results in different deflection angles relative to the longitudinal axis of hollow elongate shaft (180). Therefore, an operator may selectively articulate bendable distal end at a variety of deflection angles through a plurality of thermal fluid temperatures controlled by fluid circulation assembly (262). Steering member (266) may include a pre-formed nitinol bi-phase wire, strip or foil. If steering member (266) is made with a pre-formed nitinol bi-phase material, distal bendable end (202) may obtain a straight angle relative to the longitudinal axis of shaft (180), and two bent angles. Alternatively, steering member (266) may comprise a bi-metallic wire, strip or foil composition. If steering member (266) is made with a bi-metallic material, distal bendable end (202) may obtain a straight angle relative to the longitudinal axis of shaft (180) as well as a plurality of bent angles. Steering member (266) may be made out of any suitable combination of materials designed to convert temperature change into mechanical displacement.

In exemplary use, an operator may place the distal end of dilation catheter (200) and distal articulation assembly (256) within the nasal cavity of a patient. The operator may desire to articulate the inserted bendable distal end (202) of shaft (180) in order to align the tip of bendable distal end (202) with a targeted ostium or other drainage passageway of the patient. The operator may then adjust fluid circulation assembly to heat/cool thermal fluid and pump thermal fluid through fluid tubes (263, 265), which in turn articulates bendable distal end (202) to align with the targeted ostium or other drainage passageway of the patient (similar to that shown from the transition of FIG. 8 to FIG. 10). With the tip of bendable distal end (202) aligned with the targeted ostium or other drainage passageway of the patient, the operator may further insert bendable distal end (202) into the targeted ostium such that dilator (220) is within the targeted ostium or other drainage passageway. It should be understood steering member (266) may not only articulate bendable distal end (202), but may also provide increased stiffness, torquability, and steerability such that bendable distal end (202) may be more easily inserted into the targeted ostium or other drainage passageway. With dilator (220) within the targeted ostium or other drainage passageway, the operator may inflate dilator (202) via communication fluid and inflation lumen (184). With the targeted ostium or other drainage passageway dilated, the operator may deflate dilator (202) and remove dilation catheter (200) from the patient.

V. Exemplary Alternative Guide Catheter with Distal Articulation Assembly

In some instances, it may be desirable to articulate/bend the distal end of a guide catheter from the longitudinal axis defined by the rest of the guide catheter. It may further be desirable to selectively articulate/bend the distal end of a guide catheter during a dilation procedure at various angles while the distal end of the guide catheter is adjacent to a targeted area. In other words, it may be desirable to bend the distal end of the guide catheter while the guide catheter is within an anatomical passageway of a patient. Selective articulation/bending of the distal end of a guide catheter during a procedure may provide better steering capabilities within a nasal cavity of a patient, allowing an operator to more easily position a dilator within a targeted area. For instance, the operator may initially insert the catheter into the patient's nasal cavity while the catheter is in a straight configuration; then bend the distal end of the catheter after the catheter is positioned in the patient's nasal cavity. The bend angle may be selectively customized to facilitate access to a drainage passageway associated with a particular paranasal sinus cavity. For instance, the operator may selectively adjust the bend angle to access a drainage passageway associated with a frontal sinus, a maxillary sinus, a sphenoid sinus, or an ethmoid sinus. The following is an exemplary guide catheter having distal articulation/bending features configured to deflect the distal end of a guide catheter located adjacent to a targeted area within a patient.

FIGS. 14-15 show an exemplary handle assembly (340) connected to an exemplary guide catheter assembly (300). Handle assembly (340) and guide catheter assembly (300) may be readily incorporated into dilation catheter system (10) in place of guide catheter (30) described above. Handle assembly (340) includes a body (342) and a balloon catheter actuation assembly (344). Guide catheter assembly (300) includes a guide catheter (301) and an articulation assembly (370). As will be described in greater detail below, articulation assembly (370) is configured to actuate relative to body (342) of handle assembly (340) in order to articulate/bend a bendable distal end (320) of guide catheter (301) from the longitudinal axis defined by the rest of guide catheter (301).

Body (342) is dimensioned such that an operator may grasp body (342) with one hand. An open proximal end (360) of guide catheter (301) is fixed to the distal end of body (342). Balloon catheter actuation assembly (344) is slidably coupled to body (342). Balloon catheter actuation assembly (344) is also coupled to shaft (18) of dilation catheter (20) such that translation of balloon catheter actuation assembly (344) relative to body (342) also actuates dilation catheter (20) relative to body (342). Because open proximal end (360) of guide catheter (301) is fixed to body (342), translation of balloon catheter actuation assembly (344) also actuates dilation catheter (20) relative to guide catheter (301).

Main body (302) of guide catheter (301) defines a lumen that is configured to slidably receive dilation catheter (20), such that guide catheter (301) may guide dilator (22) through bendable distal end (320) and open distal tip (308). Therefore, distal translation of balloon catheter actuation assembly (344) relative to body (342) may cause dilator (22) to exit open distal tip (308); while proximal translation of balloon catheter actuation assembly (344) relative to body (342) may cause dilator (22) to re-enter open distal tip (308). It should be understood that shaft (18) of dilation catheter (20) is sufficiently flexible that dilation catheter (20) may exit open distal tip (308) at substantially the same angle as defined by bendable distal end (320). Therefore, articulating/bending bendable distal end (320) of guide catheter (301) relative to the longitudinal axis defined by the rest of guide catheter (301) may affect the exit angle of dilator (22).

Balloon catheter actuation assembly (344) may also be configured to rotate dilation catheter (20) about the longitudinal axis defined by shaft (18). Balloon catheter actuation assembly (344) may further include any other suitable features obvious to one having ordinary skill in the art in view of the teachings herein.

Articulation assembly (370) includes a slide (372), an annular array of splines (374), and a resilient slide wire (376). Slide (372) is slidably coupled to annular array of splines (374). Annular array of splines (374) are attached to body (342) of handle assembly (340) such as to fix splines (374) relative to open proximal end (360) of guide catheter (301). Splines (374) are configured to rotationally lock slide (372) such that slide (372) may not rotate relative to main body (302) of guide catheter (301).

Figure 16:
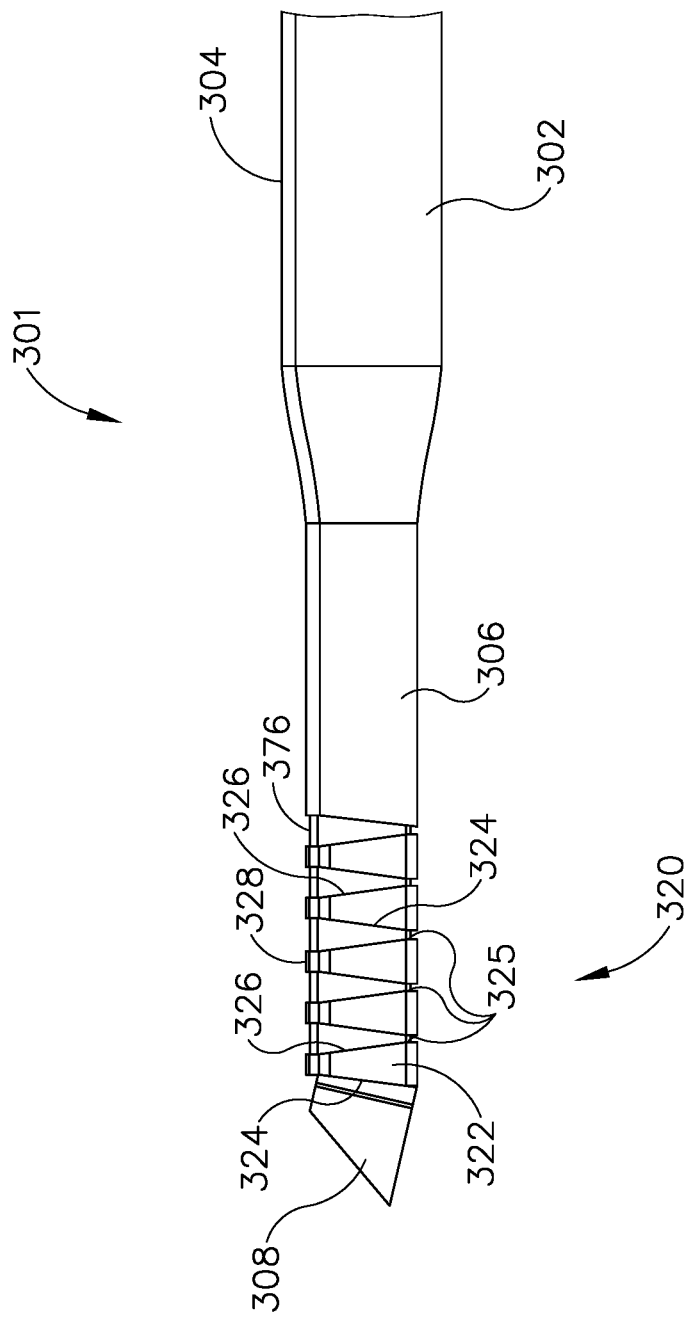
FIG. 16 depicts a side elevational view of the bendable distal end of the guide catheter of the guide catheter assembly of FIG. 14, where the bendable distal end is in the second, straight, configuration.

The proximal end of resilient slide wire (376) is fixed to the distal end of slide (372) so that actuation of slide (372) relative to main body (302) of guide catheter (301) causes actuation of resilient slide wire (376) relative to main body (302) of guide catheter (301). The distal end of resilient slide wire (376) is fixed to a portion of bendable distal end (320). The distal end of resilient slide wire (376) is sufficiently flexible to bend from a straight configuration (as shown in FIGS. 15-16) to a curved configuration (as shown in FIG. 14) in response to external forces. Additionally, resilient slide wire (376) is sufficiently resilient to return to a relaxed, straight, position as shown in FIG. 16, when no external forces are acting on resilient slide wire (376). As will be described in greater detail below, the flexible and resilient nature of resilient slide wire (376) will allow bendable distal end (320) to articulate to a bent configuration relative to the longitudinal axis defined by main body (302), as well as to force bendable distal end (320) to return to a straight configuration relative to the longitudinal axis defined by main body (302), depending on the presence of external forces.

Figure 17:
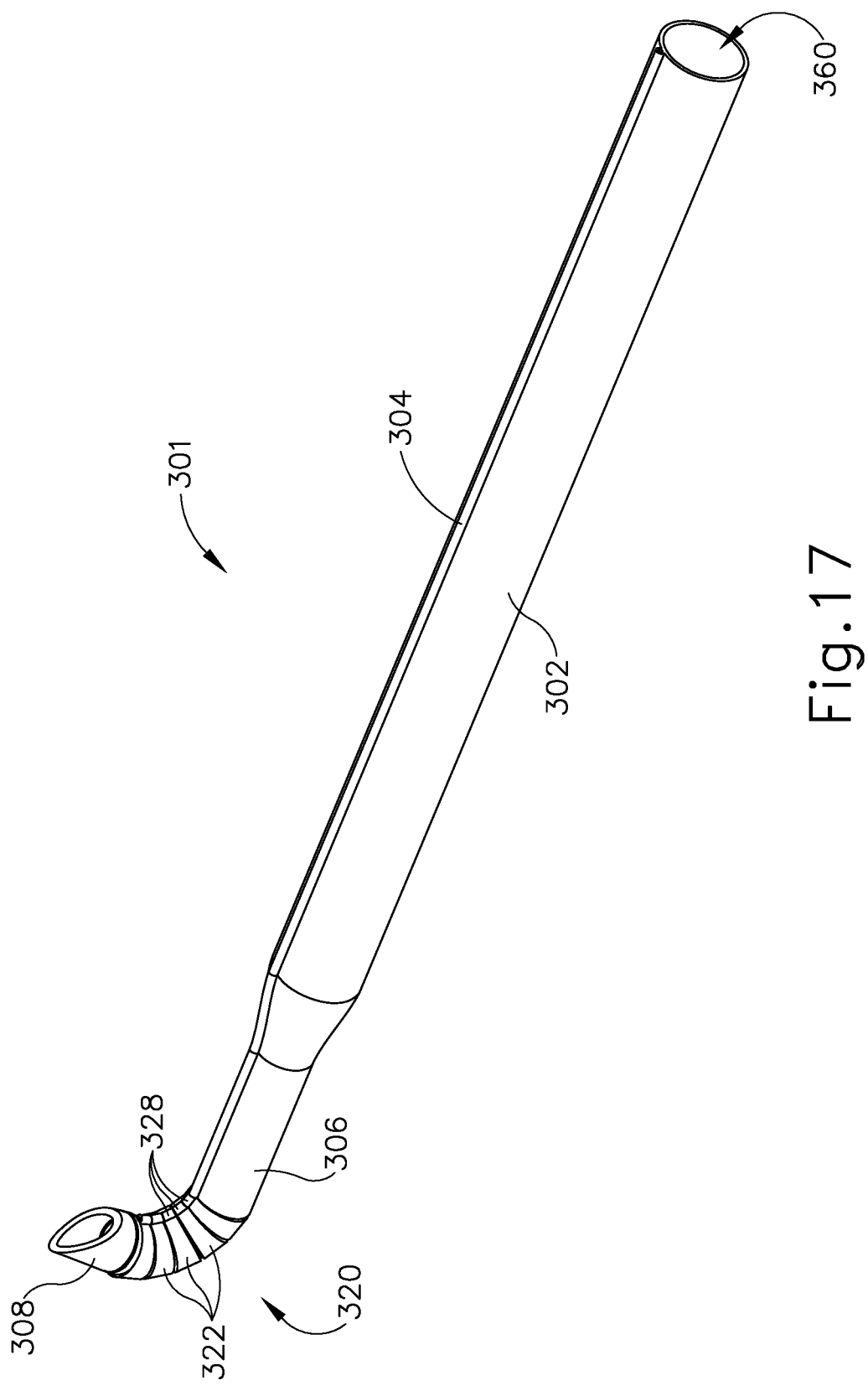
FIG. 17 depicts a perspective view of the distal end of the guide catheter of FIG. 16, where the bendable distal end is in the first, bent, configuration.

As best seen in FIGS. 16-17, guide catheter (301) includes main body (302), a rigid distal portion (306) extending distally from main body (302), bendable distal end (320), open distal tip (308), and a slide wire lumen (304) extending along main body (302) and rigid distal portion (306). Bendable distal end (320) extends distally from rigid distal portion (306) while open distal tip (308) is distally attached to bendable distal end (320). Therefore, bendable distal end (320) is located between rigid distal portion (306) and open distal tip (308). Slide wire lumen (304) extends along main body (302) and rigid distal portion (306). Slide wire lumen (304) is dimensioned to slidably house a portion of slide wire (376). Slide wire lumen (304) acts as a guide for slide wire (376).

Bendable distal end (320) includes a plurality of rotating members (322) extending from rigid distal portion (306) to open distal tip (308). Adjacent rotating members (322) are rotatably connected to each other via living hinges (325). Each rotating member (322) includes an angled distal face (324), an angled proximal face (326), and a slide wire channel (328). As will be discussed in greater detail below, distal faces (324) and proximal faces (326) of adjacent rotating members (322) are configured to contact each other in order to further encourage rotation of respective rotating members (322) about living hinges (325). While in the current example, living hinges (325) are used to connect adjacent rotating members (322), any other suitable connections may be used as would be apparent to one having ordinary skill in the art in view of the teachings herein.

Slide wire channel (328) is dimensioned to house slide wire (376). In particular, slide wire (376) is fixed to slide wire channel (328) of the distal-most rotating member (322); while slide wire (376) is slidable relative to all other slide wire channels (328). Slide wire (376) is fixed relative to the distal-most rotating member (322) in order to encourage the distal-most rotating member (322) to rotate relative to adjacent rotating member (322) via living hinge (325) during actuation of slide (372) relative to splines (374).

In exemplary use, an operator may proximally translate slide (372) in order to articulate/bend bendable distal end (320) from the position shown in FIG. 15 to the position shown in FIG. 14. Proximal translation of slide (372) encourages proximal translation of slide wire (376). Because the distal end of slide wire (376) is fixed to the distal-most rotating member (322), proximal face (326) of the distal most rotating member (322) rotates toward distal face (324) of the adjacent rotating member (322) via the respective living hinge (325) so that proximal face (326) and distal face (324) make contact with each other. Further proximal translation of slide wire (376) rotates the second most distal rotating member (322) via contact between proximal face (326) of distal-most rotating member (322) and distal face (324) of second distal most rotating member (322). Therefore, as slide wire (376) translates proximally, further contact between distal faces (324) and proximal faces (326) of adjacent rotating members (322) encourages rotating of adjacent rotating members (322) via living hinges (325).

As mentioned above, slide wire (376) is also housed within slide wire channels (328) of rotating members (322). Therefore, as rotating members (322) rotate relative to each other via living hinges (325) from the position shown in FIG. 15 to the position shown in FIG. 14, slide wire channels (328) also rotate. This rotation of slide wire channels (328) imparts an external force onto slide wire (376), causing the portion of slide wire (376) extending along bendable distal end (320) to conform to the angle defined by bendable distal end (320), similar to that shown in FIGS. 14 and 17.

An operator may distally translate slide (372) in order to articulate/bend bendable distal end (320) from the position shown in FIG. 14 to the position shown in FIG. 15. Distal translation of slide (372) encourages distal translation of slide wire (376). Because the distal end of slide wire (376) is fixed to the distal most rotating member (322), proximal face (326) of the distal most rotating member (322) rotates away from distal face (324) of the adjacent rotating member (322) via the respective living hinge (325). The resilient nature of slide wire (376) urges toward a natural, straight configuration, which encourages rotating members (322) to further rotate via living hinges (325) toward a straight configuration such that adjacent distal faces (324) and adjacent proximal faces (326) are no longer in contact with each other.

Therefore, an operator may translate slide (372) proximally or distally in order to encourage bendable distal end (320) to articulate relative to the longitudinal axis defined by main body (302) of guide catheter (301). Slide (372) may be locked in a longitudinal position relative to annular splines (374) in order to encourage bendable distal end (320) to remain in a fixed articulated/bent position relative to the longitudinal axis defined by main body (302) of guide catheter (301). In exemplary use, slide (732) may be located externally from a patient while bendable distal end (320) may be located within a patient. Therefore, an operator may selectively articulate/bend bendable distal end (320) via actuation of slide (372), even though bendable distal end (320) is located within a patient.

The distal most rotating member (322) may be fixed to the distal end of slide wire (376) via adhesives, an interference fit, or any other suitable means as would be apparent to one having ordinary skill in the art in view of the teachings herein. In the current example, slide wire (376) is fixed to the most distal rotating member (322) in the plurality of rotating members (322). However, slide wire (376) may be fixed to any other suitable location of guide catheter (301) as would be apparent to one having ordinary skill in the art in view of the teachings herein. As a mere example, the distal end of slide wire (376) may be fixed to open distal tip (308).

VI. Exemplary Alternative Distal Tips with Expandable Portions

In some instances, it may be desirable to enable distal tip (308) to transition between a relatively large size and a relatively small size. For instance, the relatively small size may be desirable during insertion and positioning of distal tip (308) within the nasal cavity. The relatively large size may be desirable to accommodate exit of dilator (22) through distal tip without providing excessive frictional contact. However, if open distal tip (308) is too large, guidewire (50) and/or dilator catheter (20) may not exit open distal tip (308) as precisely as desired. In other words, open distal tip (308) may be so large that it does not properly contact guidewire (50) and/or dilator catheter (20) in order to guide guidewire (50) and/or dilator catheter (20) toward a desired location. Therefore, it may be desirable to have a distal tip (308) that is capable of transitioning between a narrow configuration and an expanded configuration. The narrow configuration may be dimensioned to properly contact a guidewire (50) and/or dilator catheter (20) in order to guide guidewire (50) and/or dilator catheter (20) toward a desired location; while the expanded configuration may allow dilator (22) to properly exit the distal tip without damaging dilator (22) through excessive frictional contact. The following are merely illustrative examples of such distal tips.

FIG. 18 shows an alternative distal tip (400) that may be readily incorporated into dilation catheter system (10) described above. Distal tip (400) includes an upper portion (404) and a lower portion (406) defining a truncated distal face (402), an oval pathway (409), and a slot (408). Upper portion (404) and lower portion (406) are sufficiently resilient to expand and contract between a narrow configuration and an expanded configuration in response to camming between an interior of distal tip (400) and dilator (22) as dilation catheter (20) is translated relative to distal tip (400). Upper portion (404) and lower portion (406) may expand and contract in part due to the formation of slot (408), which also fluctuates in size during expansion and contraction. Truncated distal face (402) and oval pathway (409) may be dimensioned to allow for distal tip (400) to be better placed adjacent to a targeted anatomical passageway. Because upper portion (404) and lower portion (406) may expand and contract in response to camming with dilator (22), oval pathway (409) may be dimensioned smaller than a tip not having expanding capabilities. Therefore, when distal tip (400) is in a narrow configuration, guidewire (50) and/or dilator catheter (20) may protrude from distal tip (400) with greater precision than a larger tip. Additionally, expansion of distal tip (400) may further allow for dilator (22) to exit distal tip with less probability of damaging dilator due to frictional contact between distal tip (400) and dilator (22).

FIG. 19 shows another alternative distal tip (410) that may be readily incorporated into dilation catheter system (10) described above. Distal tip (410) includes an upper portion (414) and a lower portion (416) defining a slanted distal face (412), an annular pathway (419), and a slot (418). Similar to alternative distal tip (400) described above, upper portion (414) and lower portion (416) are sufficiently resilient to expand and contract between a narrow configuration and an expanded configuration in response to camming between an interior of distal tip (410) and dilator (22) as dilation catheter (20) is translated relative to distal tip (410). Upper portion (414) and lower portion (416) may expand and contract in part due to the formation of slot (418), which also fluctuates in size during expansion and contraction. Slanted distal face (412) and annular pathway (419) may be dimensioned to allow for distal tip (410) to be better placed adjacent to a targeted anatomical passageway. Because upper portion (414) and lower portion (416) may expand and contract in response to camming with dilator (22), annular pathway (419) may be dimensioned smaller than a tip not having expanding capabilities. Therefore, when distal tip (410) is in a narrow configuration, guidewire (50) and/or dilator catheter (20) may protrude from distal tip (410) with greater precision than a larger tip. Additionally, expansion of distal tip (410) may further allow for dilator (22) to exit distal tip with less probability of damaging dilator due to frictional contact between distal tip (410) and dilator (22).

FIG. 20 shows another alternative distal tip (420) that may be readily incorporated into dilation catheter system (10) described above. Distal tip (420) includes an upper portion (424) and a lower portion (426) defining a distal face (422), a pathway (429), a slot (428) terminating distally into a circular cutout (425), and a cutout (427) extending from circular cutout (425) toward upper portion (424). Similar to alternative distal tip (400, 410) described above, upper portion (424) and lower portion (426) are sufficiently resilient to expand and contract between a narrow configuration and an expanded configuration in response to camming between an interior of distal tip (420) and dilator (22) as dilation catheter (20) is translated relative to distal tip (420). Circular cutout (425) and cutout (427) may help facilitate easier expansion of upper portion (424) and lower portion (426). Therefore, upper portion (424) and lower portion (426) may expand and contract in part due to the formation of slot (428) and cutouts (425, 427), which also may fluctuate in size during expansion and contraction. Distal face (422) and annular pathway (429) may be dimensioned to allow for distal tip (420) to be better placed adjacent to a targeted anatomical passageway. Because upper portion (424) and lower portion (426) may expand and contract in response to camming with dilator (22), pathway (429) may be dimensioned smaller than a tip not having expanding capabilities. Therefore, when distal tip (420) is in a narrow configuration, guidewire (50) and/or dilator catheter (20) may protrude from distal tip (420) with greater precision than a larger tip. Additionally, expansion of distal tip (420) may further allow for dilator (22) to exit distal tip with less probability of damaging dilator due to frictional contact between distal tip (420) and dilator (22).

FIG. 21 shows another alternative distal tip (430) that may be readily incorporated into dilation catheter system (10) described above. Distal tip (430) includes an upper portion (434) and a lower portion (436) defining a distal face (432), a pathway (439) and, a slot (438) terminating distally into a circular cutout (435). Similar to alternative distal tip (400, 410, 420) described above, upper portion (434) and lower portion (436) are sufficiently resilient to expand and contract between a narrow configuration and an expanded configuration in response to camming between an interior of distal tip (430) and dilator (22) as dilation catheter (20) is translated relative to distal tip (430). Circular cutout (435) may help facilitate easier expansion of upper portion (434) and lower portion (436). Therefore, upper portion (434) and lower portion (436) may expand and contract in part due to the formation of slot (438) and cutout (435), which also may fluctuate in size during expansion and contraction. Distal face (432) and annular pathway (439) may be dimensioned to allow for distal tip (430) to be better placed adjacent to a targeted anatomical passageway. Because upper portion (434) and lower portion (436) may expand and contract in response to camming with dilator (22), pathway (439) may be dimensioned smaller than a tip not having expanding capabilities. Therefore, when distal tip (430) is in a narrow configuration, guidewire (50) and/or dilator catheter (20) may protrude from distal tip (430) with greater precision than a larger tip. Additionally, expansion of distal tip (430) may further allow for dilator (22) to exit distal tip with less probability of damaging dilator due to frictional contact between distal tip (430) and dilator (22).

VII. Exemplary One-Handed Handle Assemblies with Independent Balloon Catheter and Guidewire Controls In some instances, it may be desirable to grasp a portion of dilation catheter system (10) that controls the location of dilation catheter (20) and guidewire (50) with one hand, while also maintaining the capability of actuating dilation catheter (20) and guidewire (50) independently from each other with the same hand. FIGS. 22-25 show exemplary handle assemblies with such capabilities.

Figure 22:
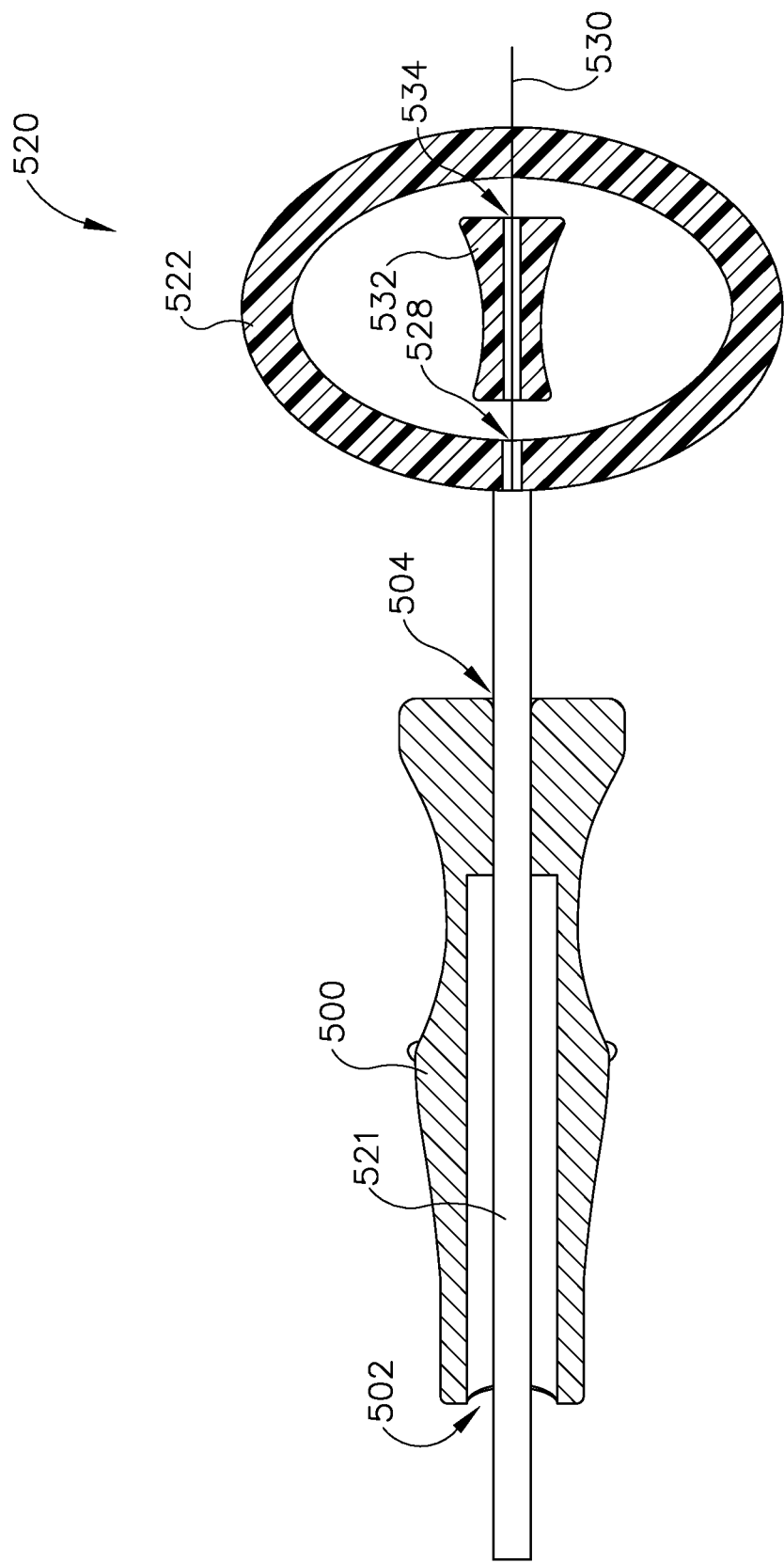
FIG. 22 depicts a cross-sectional top view of an exemplary handle actuation assembly that may be readily incorporated into the dilation catheter system of FIG. 1.
Figure 23:
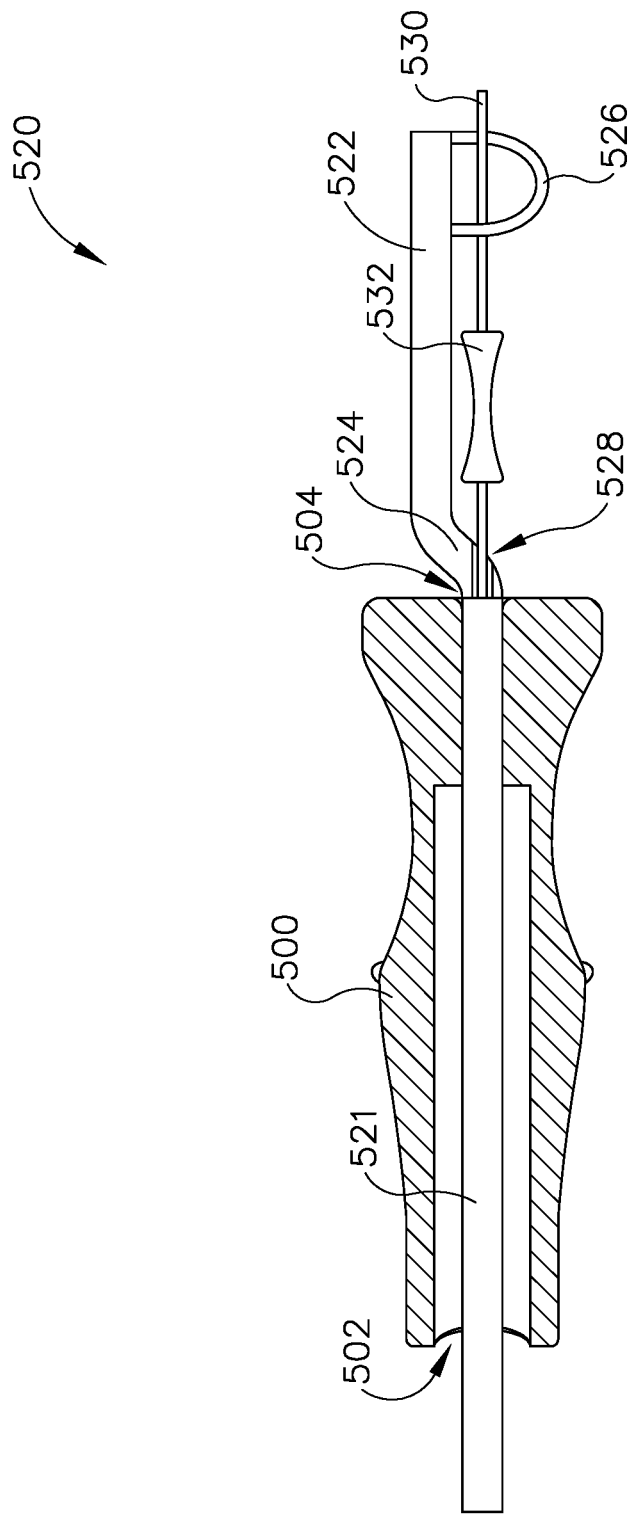
FIG. 23 depicts a cross-sectional side view of the handle actuation assembly of FIG. 22.

FIGS. 22-23 show an exemplary actuation assembly (520) coupled to an exemplary handle assembly (500), both of which are configured to be controlled and manipulated with one hand. Handle assembly (500) defines a distal channel (502) and a proximal channel (504), both of which are connected to each other in order to slidably house a balloon catheter (521) of exemplary actuation assembly (520).

Actuation assembly (520) includes a balloon catheter handle (522) fixed to balloon catheter (521), and a guidewire grip (532) selectively fixed to a guidewire (530). Guidewire (530) and balloon catheter (521) may be substantially similar to guidewire (50) and dilation catheter (20) described above, with differences described below.

Balloon catheter handle (522) is a circular body with a hollow interior designed to be easily grasped by an operator. Balloon catheter handle (522) defines a guidewire path (528) that may receive guidewire (530) and allow guidewire (530) to travel through a lumen defined by balloon catheter (521). It should be understood that guidewire (530) may actuate and rotate independently of handle (500) and balloon catheter handle (520). Additionally, it should be understood that balloon catheter handle (520) and balloon catheter (521) may unitarily rotate and actuate relative to guidewire (530) and handle (500). A rigid loop (526) extends from balloon catheter handle (522) to surround a portion of guidewire (530). Guidewire grip (530) may travel through rigid loop (526) such that guidewire grip (530) may be replaced if desired. Balloon catheter handle (522) also includes an elevated stem (524) which creates a vertical distance between guidewire grip (532) and balloon catheter handle (522). Therefore, an operator may more easily grasp the desired balloon catheter handle (522) or guidewire grip (532) without confusion. An operator may actuate balloon catheter (521) by moving balloon catheter handle (522) toward and away from handle (500). Similarly, an operator may rotate balloon catheter (521) by rotating balloon catheter handle (522) relative to handle (500). Additionally, guidewire (530) may rotate and actuate via guidewire grip (532).

Figure 24:
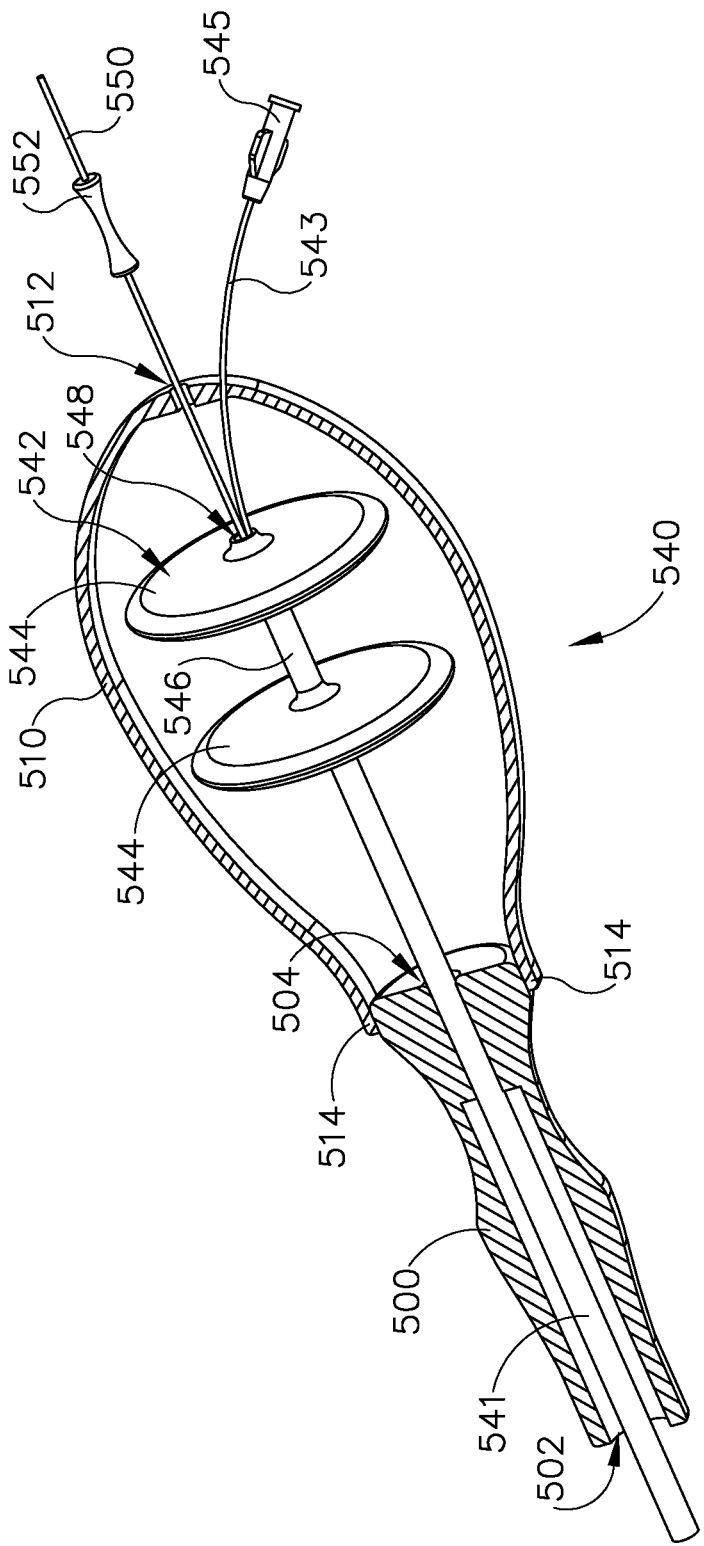
FIG. 24 depicts a partial cross-sectional perspective view of another exemplary handle actuation assembly that may be readily incorporated into the dilation catheter system of FIG. 1.

FIG. 24 shows handle assembly (500) coupled to alterative exemplary actuation assembly (540). Actuation assembly (540) and handle assembly (500) are configured to be controlled and manipulated with one hand. Distal channel (502) and proximal channel (504) are dimensioned to slidably house a balloon catheter (541) of actuation assembly (540).

Actuation assembly (540) includes a handle grip (510) fixed to handle (500) at fixed ends (514), a balloon catheter handle (542) fixed to balloon catheter (541) and inflation lumen (543), an inflation port (545), and a guidewire grip (552) selectively fixed to a guidewire (550). Guidewire (550), guidewire grip (552), and balloon catheter (541) may be substantially similar to guidewire (530), guidewire grip (532), and balloon catheter (541) described above, with differences described below. Inflation portion (545) and inflation lumen (543) are in sufficient fluid communication with balloon catheter (542) in order to provide fluid communication with a dilator (not shown) at the distal end of balloon catheter (542). Additionally, inflation lumen (543) and inflation port (545) are connected to balloon catheter (541).

Balloon catheter handle (542) includes two discs (544) connected with a hollow shaft (546), all of which define a channel (548) that receives guidewire (550) and allows guidewire (550) to travel through a lumen defined by balloon catheter (541). Discs (544) may be easily grasped by an operator's fingers while an operator simultaneously grasps handle grip (510) with their palm. Handle grip (510) also defines a guidewire channel (512) to receive guidewire. It should be understood that guidewire (550) may actuate and rotate independently of handle (500) and balloon catheter handle (540). Additionally, it should be understood that balloon catheter handle (540) and balloon catheter (541) may unitarily rotate and actuate relative to guidewire (550) and handle (500). In the current example, guidewire grip (552) is proximal in relation to handle grip (510), however this is merely optional. Guidewire grip (552) may be located within handle grip (510) adjacent to balloon catheter handle (542). An operator may actuate balloon catheter (541) by moving balloon catheter handle (542) toward and away from handle (500). Similarly, an operator may rotate balloon catheter (541) by rotating balloon catheter handle (542) relative to handle (500). Additionally, guidewire (550) may rotate and actuate via guidewire grip (552).

Figure 25:
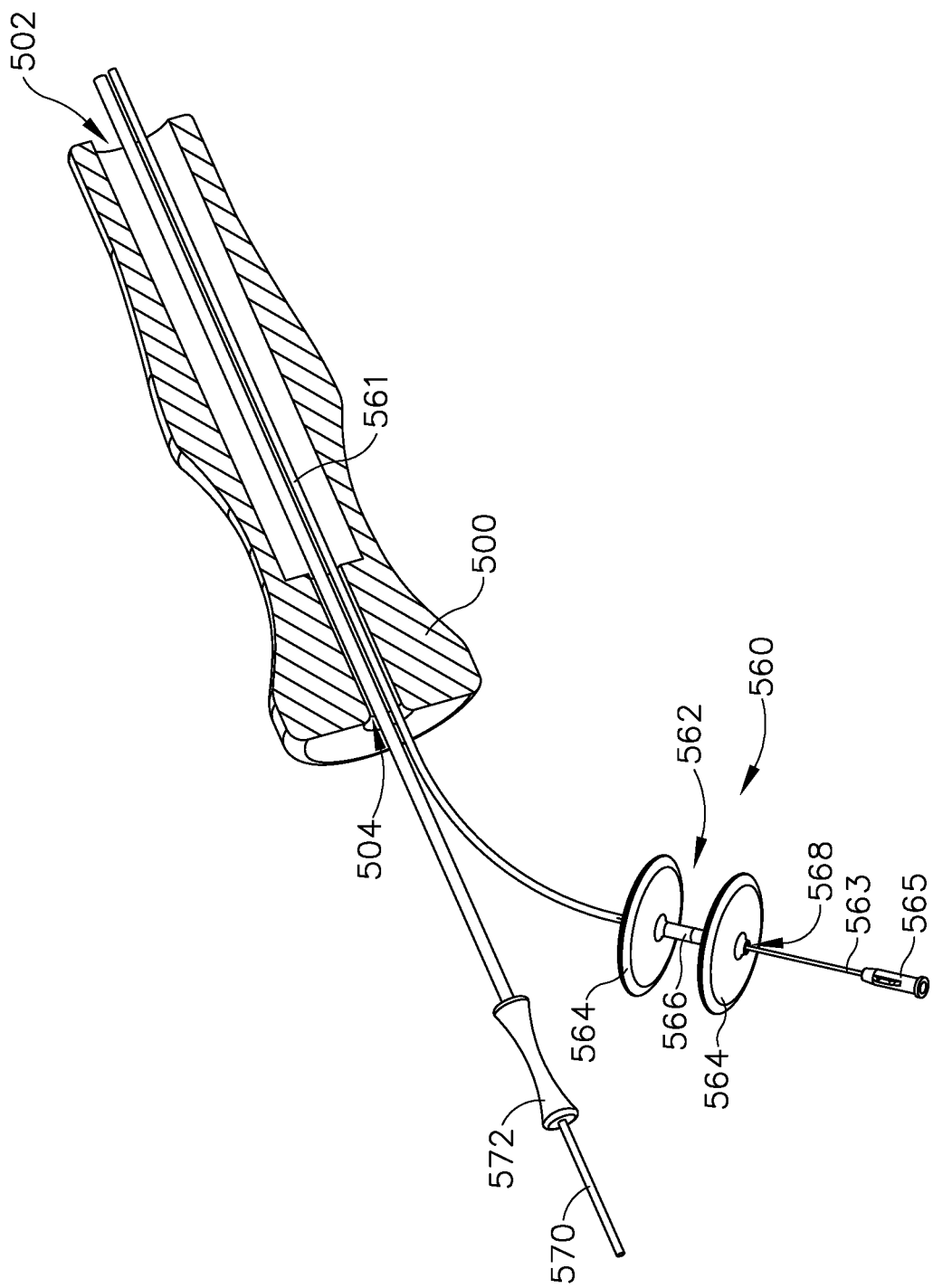
FIG. 25 depicts a partial cross-sectional perspective view of another exemplary handle actuation assembly that may be readily incorporated into the dilation catheter system of FIG. 1.

FIG. 25 shows handle assembly (500) coupled to another alternative exemplary actuation assembly (560). Actuation assembly (560) and handle assembly (500) are configured to be controlled and manipulated with one hand. Distal channel (502) and proximal channel (504) are dimensioned to slidably house a balloon catheter (561) and a guidewire (570) of actuation assembly (560). In previous examples, guidewire (530, 550) was slidably housed within a lumen of respective balloon catheter (521,541). However, in the current example, guidewire (570) is independently housed within handle (500).

Actuation assembly (560) includes a balloon catheter handle (562) fixed to balloon catheter (561) and inflation lumen (563), an inflation port (565), and a guidewire grip (572) selectively fixed to guidewire (570). Balloon catheter handle (562) includes a pair of discs (564) connected to a hollow shaft (566) defining a channel (568), inflation lumen (563) and inflation port (565); all of which may be substantially similar to discs (544), hollow shaft (546), channel (548), inflation lumen (563) and inflation port (545) described above. The primary difference between actuation assembly (560) and actuation assembly (540) described above, is actuation assembly (560) does not have a handle grip (510), and guidewire (570) does not travel through a lumen defined by balloon catheter (561). However, all other functionality may be substantially similar to actuation assembly (540) described above. Therefore, guidewire (570) may be controlled by guidewire grip (572) independently of balloon catheter handle (562). Additionally, balloon catheter handle (562) may be controlled independently of guidewire grip (572) and guidewire (570).

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a dilation catheter comprising: (i) a shaft defining a longitudinal axis, a central lumen, a fluid transfer lumen, a lead lumen, and a return lumen, wherein the shaft comprises: (A) a proximal end, and (B) a flexible distal end configured to bend relative to the longitudinal axis, wherein the central lumen, the lead lumen, and the return lumen converge at a common location near the flexible distal end, and (ii) a dilator in fluid communication with the fluid transfer lumen, wherein the dilator is configured to transition from a non-expanded state to an expanded state; and (b) an articulation assembly configured to bend the flexible distal end relative to the longitudinal axis, wherein the articulation assembly comprises: (i) an articulation drive wherein the articulation drive extends from the lead lumen and the return lumen through the common location, and (ii) a steering member housed within the central lumen, wherein the steering member extends within the common location, wherein the articulation drive is configured to bend the steering member relative to the longitudinal axis.

Example 2

The apparatus of Example 1, wherein the articulation assembly further comprises a control unit configured to activate the articulation drive to bend the steering member.

Example 3

The apparatus of Example 2, wherein the articulation drive comprises a lead resistive element and a return resistive element, wherein the lead resistive element extends through the lead lumen, wherein the return resistive element extends through the return lumen.

Example 4

The apparatus of Example 3, wherein the control unit comprises a positive lead in communication with the lead resistive element, and a negative lead in communication with the return resistive element.

Example 5

The apparatus of Example 4, wherein the control unit is configured to drive a preselected current through the lead resistive element and the return resistive element in order to bend the steering member relative to the longitudinal axis.

Example 6

The apparatus of Example 5, wherein the control unit comprises a constant voltage variable resistor device.

Example 7

The apparatus of any one or more of Examples 5 through 6, wherein the control unit comprises a resistance bridge.

Example 8

The apparatus of any one or more of Examples 2 through 7, wherein the control unit comprises a fluid circulation assembly.

Example 9

The apparatus of Example 8, wherein the articulation drive comprises a lead fluid tube extending through the lead lumen, and a return fluid tube extending through the return lumen, wherein the lead fluid tube and the return fluid tube are in fluid communication with each other.

Example 10

The apparatus of Example 9, wherein the lead fluid tube is in fluid communication with the fluid circulation assembly, wherein the return fluid tube is in fluid communication with the fluid circulation assembly.

Example 11

The apparatus of Example 10, wherein the fluid circulation assembly is configured to pump a thermal fluid through the lead fluid tube and the return fluid tube.

Example 12

The apparatus of Example 11, wherein the fluid circulation assembly is configured to heat or cool the thermal fluid to a preselected temperature.

Example 13

The apparatus of any one or more of Examples 1 through 12, wherein the steering member is in thermal communication with the articulation drive at the common location.

Example 14

The apparatus of any one or more of Examples 1 through 13, wherein the steering member comprises a pre-formed nitinol bi-phase material.

Example 15

The apparatus of any one or more of Examples 1 through 14, wherein the steering member comprises a bi-metallic material.

Example 16

An apparatus comprising: (a) a guide catheter assembly, wherein the guide catheter assembly comprises: (i) a body extending from an open proximal end to a rigid distal portion, wherein the body defines a longitudinal axis, and (ii) a bendable distal portion configured to bend relative to the longitudinal axis; and (b) an actuation assembly configured to bend the bendable distal portion relative to the longitudinal axis, wherein the actuation assembly comprises: (i) a movable member associated with the body of the guide catheter, and (ii) a resilient member extending from the movable member and attached to the bendable distal portion, wherein the resilient member is configured to bend the bendable distal portion in response to movement of the moveable member.

Example 17

The apparatus of Example 16, wherein the guide catheter further comprises an open distal tip attached to a distal end of the bendable distal portion, wherein the open distal tip comprises a first portion and second portion, wherein the first portion and the second portion define a slot, wherein the first portion and the second portion are configured to expand relative to each other in order to expand the slot.

Example 18

The apparatus of any one or more of Examples 16 through 17, wherein the bendable distal portion comprises of plurality of rotating members configured to cam against each other to bend relative to the longitudinal axis.

Example 19

The apparatus of any one or more of Examples 16 through 17, wherein the main body defines an actuation assembly lumen, wherein the actuation assembly lumen houses the resilient member.

Example 20

An apparatus comprising: (a) a balloon catheter actuation assembly comprising:
(i) a balloon catheter comprising a proximal end and a distal end, and (ii) a balloon catheter handle fixed to the proximal end of the balloon catheter, wherein the balloon catheter handle defines a channel; and (b) a guidewire actuation assembly comprising: (i) a guidewire extending through the channel, and (ii) a guidewire grip, wherein the guidewire grip is configured to selectively couple with the guidewire, wherein the guidewire grip and the guidewire are configured to unitarily actuate relative to the balloon catheter actuation assembly, wherein the balloon catheter actuation assembly is configured to unitarily actuate relative to the guidewire actuation assembly.

IX. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a dilation catheter comprising:
        (i) a shaft defining a longitudinal axis, a central lumen, a fluid transfer lumen, a lead lumen, and a return lumen, wherein the shaft comprises:
            (A) a proximal end, and
            (B) a flexible distal end configured to bend relative to the longitudinal axis,
            wherein the central lumen, the lead lumen, and the return lumen converge at a common point near the flexible distal end, and
        (ii) a dilator in fluid communication with the fluid transfer lumen, wherein the dilator is configured to transition from a non-expanded state to an expanded state; and
    (b) an articulation assembly configured to bend the flexible distal end relative to the longitudinal axis, wherein the articulation assembly comprises:
        (i) an articulation drive wherein the articulation drive extends from the lead lumen and the return lumen through the common point, and
        (ii) a steering member housed within the central lumen, wherein the steering member terminates within the central lumen proximal to the common point without physically contacting the articulation drive, wherein the articulation drive is in sufficient thermal communication with the steering member such that the articulation drive is configured to bend the steering member relative to the longitudinal axis.

2. The apparatus of claim 1, wherein the articulation assembly further comprises a control unit configured to activate the articulation drive to bend the steering member.

3. The apparatus of claim 2, wherein the articulation drive comprises a lead resistive element and a return resistive element, wherein the lead resistive element extends through the lead lumen, wherein the return resistive element extends through the return lumen.

4. The apparatus of claim 3, wherein the control unit comprises a positive lead in communication with the lead resistive element, and a negative lead in communication with the return resistive element.

5. The apparatus of claim 4, wherein the control unit is configured to drive a preselected current through the lead resistive element and the return resistive element in order to bend the steering member relative to the longitudinal axis.

6. The apparatus of claim 5, wherein the control unit comprises a constant voltage variable resistor device.

7. The apparatus of claim 5, wherein the control unit comprises a resistance bridge.

8. The apparatus of claim 2, wherein the control unit comprises a fluid circulation assembly.

9. The apparatus of claim 8, wherein the articulation drive comprises a lead fluid tube extending through the lead lumen, and a return fluid tube extending through the return lumen, wherein the lead fluid tube and the return fluid tube are in fluid communication with each other.

10. The apparatus of claim 9, wherein the lead fluid tube is in fluid communication with the fluid circulation assembly, wherein the return fluid tube is in fluid communication with the fluid circulation assembly.

11. The apparatus of claim 10, wherein the fluid circulation assembly is configured to pump a thermal fluid through the lead fluid tube and the return fluid tube.

12. The apparatus of claim 11, wherein the fluid circulation assembly is configured to heat or cool the thermal fluid to a preselected temperature.

13. The apparatus of claim 1, wherein the steering member is in thermal communication with the articulation drive at the common location.

14. The apparatus of claim 1, wherein the steering member comprises a pre-formed nitinol bi-phase material.

15. The apparatus of claim 1, wherein the steering member comprises a bi-metallic material.

16. An apparatus comprising:
(a) a dilation catheter comprising:
  (i) a shaft defining a longitudinal axis, a central lumen, a fluid transfer lumen, a lead lumen, and a return lumen, wherein the shaft comprises a flexible distal end configured to bend relative to the longitudinal axis, wherein the central lumen, the lead lumen, and the return lumen converge at a common point near the flexible distal end, and
  (ii) a dilator in fluid communication with the fluid transfer lumen, wherein the dilator is configured to transition from a non-expanded state to an expanded state; and
(b) an articulation assembly configured to bend the flexible distal end relative to the longitudinal axis, wherein the articulation assembly comprises:
  (i) an articulation drive wherein the articulation drive extends through the lead lumen and the return lumen, and
  (ii) a steering member housed within the central lumen, wherein the steering member is not in contact with the articulation drive, wherein the articulation drive is in sufficient thermal communication with the steering member such that the articulation drive is configured to bend the steering member relative to the longitudinal axis based on a temperature of the articulation drive.

17. The apparatus of claim 16, wherein the articulation drive comprises an electrical communication wire.

18. The apparatus of claim 16, wherein the articulation drive comprises a tube configured to hold fluid.

19. The apparatus of claim 16, wherein the steering member comprises a pre-formed nitinol bi-phase material.

20. An apparatus comprising:
(a) a dilation catheter comprising:
  (i) a shaft defining a longitudinal axis, a central lumen, a fluid transfer lumen, a lead lumen, and a return lumen, wherein the shaft comprises a flexible distal end configured to bend relative to the longitudinal axis, wherein the central lumen, the lead lumen, and the return lumen converge at a common point near the flexible distal end, and
  (ii) a dilator in fluid communication with the fluid transfer lumen, wherein the dilator is configured to transition from a non-expanded state to an expanded state; and
(b) an articulation assembly configured to bend the flexible distal end relative to the longitudinal axis, wherein the articulation assembly comprises:
  (i) an articulation drive extending through the lead lumen and the return lumen, and
  (ii) a steering member housed within the central lumen, wherein the steering member is not in contact with the articulation drive, wherein the articulation drive is in sufficient thermal communication with the steering member such that the articulation drive is configured to bend the steering member relative to the longitudinal axis based on a temperature of the articulation drive.

\* \* \* \* \*